(12) United States Patent  
Wengreen

(10) Patent No.: US 10,842,949 B1
(45) Date of Patent: Nov. 24, 2020

(54) AUTO-INJECTORS FEATURING MEDICINE DELIVERY ASSURANCE

(71) Applicant: Benson Eric Wengreen, Sammamish, WA (US)

(72) Inventor: Benson Eric Wengreen, Sammamish, WA (US)

( * ) Notice: Subject to any disclaimer, the term of this patent is extended or adjusted under 35 U.S.C. 154(b) by 0 days.

(21) Appl. No.: 16/943,213

(22) Filed: Jul. 30, 2020

(51) Int. Cl.
*A61M 5/20* (2006.01)
*A61M 5/32* (2006.01)
*A61M 5/315* (2006.01)

(52) U.S. Cl.
CPC ........ *A61M 5/3275* (2013.01); *A61M 5/2033* (2013.01); *A61M 5/31528* (2013.01); *A61M 5/31571* (2013.01); *A61M 2205/0222* (2013.01)

(58) Field of Classification Search
CPC .......... A61M 5/2033; A61M 2005/206; A61M 2005/208; A61M 5/3275; A61M 5/31528; A61M 5/31571
See application file for complete search history.

(56) References Cited

U.S. PATENT DOCUMENTS

| | | | |
|---|---|---|---|
| 4,031,893 A | 6/1977 | Kaplan | |
| 4,394,863 A | 7/1983 | Bartner | |
| 4,484,910 A | 11/1984 | Sarnoff | |
| 4,640,686 A | 2/1987 | Dalling | |
| 4,678,461 A | 7/1987 | Mesa | |
| 4,795,433 A | 1/1989 | Sarnoff | |
| 4,832,682 A | 5/1989 | Sarnoff | |
| 5,085,641 A | 2/1992 | Sarnoff | |
| 5,092,843 A | 3/1992 | Monroe | |
| 5,102,393 A | 4/1992 | Sarnoff | |
| 5,354,286 A | 10/1994 | Mesa | |
| 7,449,012 B2 | 11/2008 | Young | |
| 8,048,035 B2 | 11/2011 | Mesa | |
| 9,364,611 B2 | 6/2016 | Kramer | |
| 9,427,531 B2 * | 8/2016 | Hourmand | ........ A61M 5/3257 |
| 9,724,471 B2 | 8/2017 | Edwards | |
| 9,764,091 B2 | 9/2017 | Bechmann | |
| 9,833,573 B2 | 12/2017 | Edwards | |

OTHER PUBLICATIONS

Epinephrine Auto-Injector, downloaded on Aug. 1, 2020 from https://en.wikipedia.org/wiki/Epinephrine_autoinjector.

* cited by examiner

Primary Examiner — Laura A Bouchelle

(57) ABSTRACT

Auto-injectors can deliver many different types of medicines into people. One failure mode of auto-injectors is failing to insert the needle into the patient while the medicine is propelled from the auto-injector. This error results in the medicine not entering the patient's body. An auto-injector can include a syringe and probes to prevent medicine from being propelled if the person administering the injection does not position the auto-injector correctly.

19 Claims, 27 Drawing Sheets

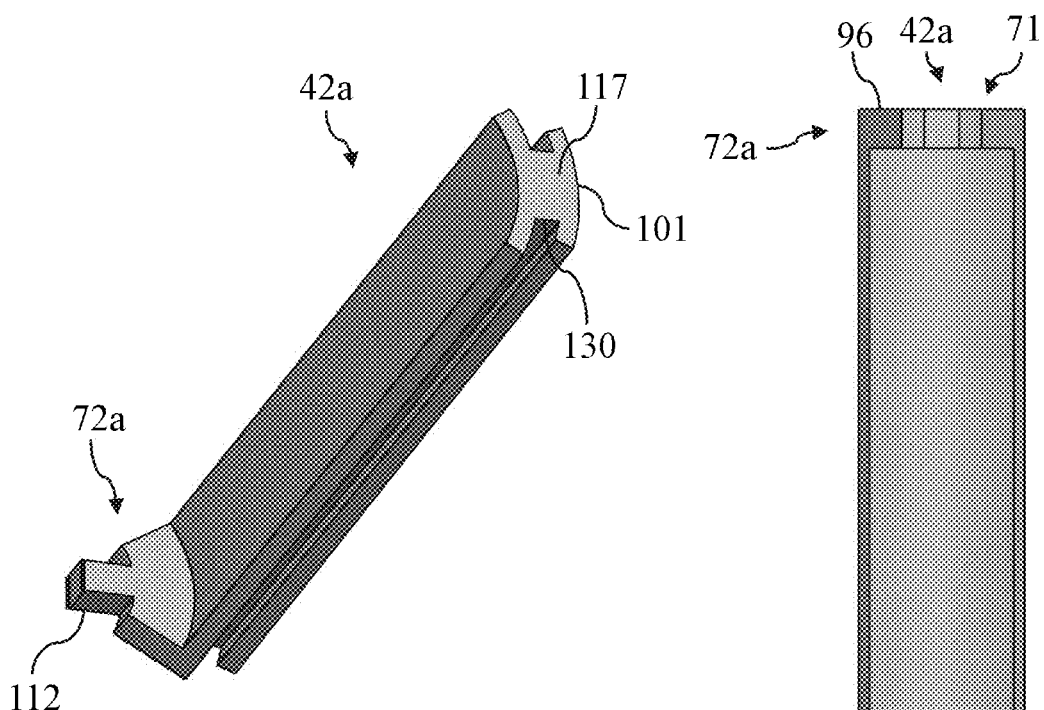
Figure 24
Figure 25
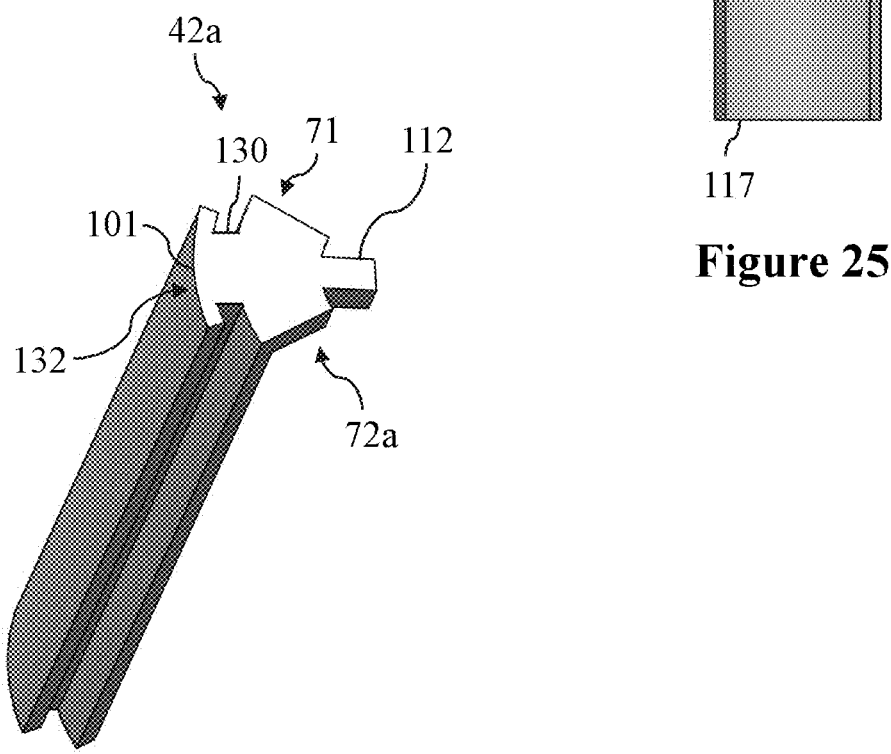
Figure 26

AUTO-INJECTORS FEATURING MEDICINE DELIVERY ASSURANCE

BACKGROUND

Field

Various embodiments disclosed herein relate to injectors. Certain embodiments relate to auto-injectors that provide medicine to a patient.

Description of Related Art

Injectors can be used to inject medicine into a person. Injectors can inject many different types of medicines.

Some injectors inject epinephrine into people suffering a severe, potentially life-threatening allergic reaction called anaphylaxis. People suffering from anaphylaxis need an injection of epinephrine immediately and often cannot wait for an ambulance or wait to arrive at a hospital to receive an injection of epinephrine. As a result, epinephrine injections are commonly administered by a person without medical training. Often, people experiencing anaphylactic shock have to inject themselves with epinephrine. Failing to administer the injection correctly, however, can have life-threatening consequences. Unfortunately, incorrect administration of epinephrine injections is far too common.

One key failure mode of these injections is failing to insert the needle into the patient while the medicine is propelled from the injector. This error results in the medicine not entering the patient's body. As a result, the medicine cannot save the patient's life. Thus, there is a need for systems and methods that preclude the release of the medicine unless the injector is properly positioned to place the needle inside the body of the person who needs the medicine.

SUMMARY

Some embodiments are directed to an injector, which can be an auto-injector used to inject medicine into a person.

In some embodiments, an injector comprises an outer housing assembly; a syringe that has a barrel, a needle, and a plunger; and a first probe that protrudes from a distal end of the outer housing assembly. The first probe can be slidably coupled to the outer housing assembly. The barrel of the syringe can hold a medicine. The plunger can be slidably coupled at least partially inside the barrel such that the plunger is configured to push the medicine out of the barrel and out of the needle (into a person). The needle can be coupled to a distal end portion of the barrel.

In some embodiments, the syringe can be coupled to the outer housing assembly such that the syringe is located at least partially inside the outer housing assembly. The syringe can be slidably coupled to the outer housing assembly to enable the syringe to move distally relative to the outer housing assembly to inject a medicine into a person.

In some embodiments, the injector comprises a second probe protruding from the distal end of the outer housing assembly and configured to move independently of the first probe; a first rod configured such that moving the first probe proximally relative to the outer housing assembly pushes the first rod proximally to unlock the first rod from the plunger; and a second rod configured to move independently of the first rod such that moving the second probe proximally relative to the outer housing assembly pushes the second rod proximally to unlock the second rod from the plunger. The injector can be configured such that unlocking both the first rod and the second rod from the plunger enables the plunger to rotate relative to the outer housing assembly such that a first spring pushes the needle distally relative to the outer housing assembly to inject a medicine into a person.

In some embodiments, the outer housing assembly comprises a radially inward protrusion configured to limit a first distal movement of the first rod. The injector can be configured to enable the first probe to continue moving distally after the radially inward protrusion limits the first distal movement of the first rod such that the first probe is configured to block access to the needle after the needle injects a medicine.

In some embodiments, the plunger comprises a first threaded portion and the outer housing assembly comprises a second threaded portion that is threadably coupled with the first threaded portion. The injector can be configured such that unlocking both the first rod and the second rod from the plunger causes a spring force of the first spring to rotate the plunger relative to the outer housing assembly due to the first threaded portion contacting the second threaded portion.

In some embodiments, an injector comprises a second spring located around at least a first portion of the plunger. The second spring can be compressed between a first radially outward protrusion of the plunger and at least one of the first probe and the second probe.

In some embodiments, a third spring is compressed between a proximal end of the outer housing assembly and at least a second portion of the first rod such that the third spring is configured to push the first rod distally relative to the outer housing assembly. The injector can be configured such that moving the first probe proximally relative to the outer housing assembly to push the first rod proximally to unlock the first rod from the plunger requires overcoming a spring force of the third spring.

In some embodiments, a proximal end of the plunger comprises at least one proximal protrusion, a proximal end of the first rod comprises a first radially inward protrusion, and the second rod comprises a second radially inward protrusion on a proximal end of the second rod.

In some embodiments, the first radially inward protrusion and the second radially inward protrusion are interlocked with the at least one proximal protrusion of the plunger such that the injector is configured so the plunger cannot rotate relative to the outer housing assembly until after the first radially inward protrusion and the second radially inward protrusion move proximally relative to the at least one proximal protrusion.

In some embodiments, an angle between the first radially inward protrusion and the second radially inward protrusion is greater than 100 degrees and less than 140 degrees. A first proximal end portion of the first rod can comprise the first radially inward protrusion. A second proximal end portion of the second rod can comprise the second radially inward protrusion.

In some embodiments, a proximal end of the plunger comprises a first proximal protrusion, a second proximal protrusion, and a third proximal protrusion. The first proximal protrusion, the second proximal protrusion, and the third proximal protrusion can form a first channel, a second channel, and a third channel.

In some embodiments, the first rod comprises a first radially inward protrusion located at least partially in the first channel such that the first radially inward protrusion blocks the plunger from rotating relative to the outer housing assembly.

In some embodiments, the second rod comprises a second radially inward protrusion located at least partially in the second channel such that the second radially inward protrusion blocks the plunger from rotating relative to the outer housing assembly.

In some embodiments, the third rod comprises a third radially inward protrusion located at least partially in the third channel such that the third radially inward protrusion blocks the plunger from rotating relative to the outer housing assembly.

In some embodiments, the injector is configured such that the plunger cannot rotate relative to the outer housing assembly to enable the needle to move distally to inject a medicine until after the first probe moves proximally and thereby pushes the first rod proximally to move the first radially inward protrusion proximally out of the first channel; the second probe moves proximally and thereby pushes the second rod proximally to move the second radially inward protrusion proximally out of the second channel; and the third probe moves proximally and thereby pushes the third rod proximally to move the third radially inward protrusion proximally out of the third channel.

In some embodiments, the first probe comprises a proximally facing end that abuts a distally facing end of the first rod. The injector can be configured such that the proximally facing end pushes the distally facing end proximally to move the first radially inward protrusion proximally out of the first channel.

In some embodiments, the first probe comprises a flex arm configured to flex to enable distal movement of the first probe and then collide with a distal face of the outer housing assembly to prevent proximal movement of the first probe.

In some embodiments, the outer housing assembly comprises a first groove and a second groove that are oriented from a distal end of the outer housing assembly to a proximal end of the outer housing assembly. The first probe can comprise a first fin slidably coupled to the first groove. The first rod can comprise a second fin slidably coupled to the second groove.

In some embodiments, the outer housing assembly comprises a first groove. The barrel can comprise a first radially outward protrusion located at least partially between the first probe and the second probe such that the first probe and the second probe limit rotation of the first radially outward protrusion relative to a first central axis of the outer housing assembly.

In some embodiments, the first probe, the second probe, and the first radially outward protrusions are slidably coupled to the first groove having a second central axis that is oriented within ten degrees of parallel to the first central axis.

In some embodiments, the first probe comprises a distally facing skin-contacting surface, a flex arm, a first radially outward protrusion, and a second radially outward protrusion, and the outer housing assembly comprises a first groove and a second groove.

In some embodiments, the flex arm is configured to flex to enable distal movement of the first probe and then collide with a distal face of the outer housing assembly to prevent proximal movement of the first probe. The first radially outward protrusion can be slidably coupled to the first groove of the outer housing assembly. The second radially outward protrusion can be slidably coupled to the second groove of the outer housing assembly.

In some embodiments, the outer housing assembly comprises a first groove, a second groove, a third groove, and a fourth groove. In some embodiments, grooves are long, narrow channels.

In some embodiments, the first probe is slidably coupled to the first groove, the second probe is slidable coupled to the second groove, the first rod is slidably coupled to the third groove, and the second rod is slidably coupled to the fourth groove such that the first probe, the second probe, the first rod, and the second rod are configured to move proximally relative to the outer housing assembly to enable the plunger to rotate relative to the outer housing assembly.

In some embodiments, the first probe comprises a first radially outward protrusion that slidably couples the first probe to the first groove. The second probe can comprise a second radially outward protrusion that slidably couples the second probe to the second groove. The first rod can comprise a third radially outward protrusion that slidably couples the first rod to the third groove. The second rod can comprise a fourth radially outward protrusion that slidably couples the second rod to the fourth groove.

In some embodiments, the first probe comprises a first L-shaped protrusion that slidably couples the first probe to the first groove. The second probe can comprise a second L-shaped protrusion that slidably couples the second probe to the second groove. The first rod can comprise a first T-shaped protrusion that slidably couples the first rod to the third groove. The second rod can comprise a second T-shaped protrusion that slidably couples the second rod to the fourth groove.

In some embodiments, the first groove, the second groove, the third groove, and the fourth groove run from a distal portion of the outer housing assembly to a proximal portion of the outer housing assembly.

In some embodiments, the outer housing assembly comprises a central axis from a distal portion of the outer housing assembly to a proximal portion of the outer housing assembly, the first groove is oriented in a first direction from the distal portion to the proximal portion, the second groove is oriented in a second direction from the distal portion to the proximal portion, the third groove is oriented in a third direction from the distal portion to the proximal portion, the fourth groove is oriented in a fourth direction from the distal portion to the proximal portion, and the first direction, the second direction, the third direction, and the fourth direction are within ten degrees of parallel to the central axis.

In some embodiments, an injector comprises an outer housing assembly; a syringe coupled at least partially inside the outer housing assembly and having a barrel, a needle, and a plunger; and a first probe protruding from a distal end of the outer housing assembly.

In some embodiments, an injector comprises a second probe protruding from the distal end of the outer housing assembly and configured to move independently of the first probe; and a third probe protruding from the distal end of the outer housing assembly and configured to move independently of the first probe and the second probe.

In some embodiments, an injector comprises a first rod configured such that moving the first probe proximally relative to the outer housing assembly pushes the first rod proximally to unlock the first rod from the plunger; a second rod configured to move independently of the first rod such that moving the second probe proximally relative to the outer housing assembly pushes the second rod proximally to unlock the second rod from the plunger; and a third rod configured to move independently of the first rod and the second rod such that moving the third probe proximally relative to the outer housing assembly pushes the third rod proximally to unlock the third rod from the plunger.

In some embodiments, an injector comprises a first spring configured to push the plunger distally relative to the outer housing assembly. The injector can be configured such that unlocking the first rod, the second rod, and the third rod from the plunger enables the plunger to move distally relative to the outer housing assembly such that the first spring pushes the plunger distally relative to the outer housing assembly to inject a medicine into a person.

Some embodiments consist of two rods such that just unlocking the first rod but not unlocking the second rod will not enable the plunger to move distally relative to the outer housing because the second rod prevents the distal movement. Thus, in some embodiments, both rods must be unlocked before the plunger can move distally relative to the outer housing to inject the medicine.

Some embodiments consist of three rods such that just unlocking the first rod and the second rod but not unlocking the third rod will not enable the plunger to move distally relative to the outer housing because the third rod prevents the distal movement. Thus, in some embodiments all three rods must be unlocked before the plunger can move distally relative to the outer housing to inject the medicine.

Some embodiments consist of more than three rods such that unlocking all the rods is necessary to enable the plunger to move distally relative to the outer housing.

In some embodiments, the injector is configured such that after the medicine is injected, the first probe, the second probe, and the third probe move distally relative to the outer housing assembly to form a sheath that blocks a distal end of the needle from punctures.

In some embodiments, the first probe, the second probe, and the third probe are spaced radially outward around a perimeter of the needle.

In some embodiments, an injector comprises a second spring located around at least a first portion of the plunger and compressed between a first radially outward protrusion of the plunger and at least one of the first probe and the second probe.

In some embodiments, an injector comprising a third spring compressed between a proximal end of the outer housing assembly and at least a second portion of the first rod such that the third spring is configured to push the first rod, the second rod, and the third rod distally relative to the outer housing assembly. The injector can be configured such that moving the first probe, the second probe, and the third probe proximally relative to the outer housing assembly to push the first rod, the second rod, and the third rod proximally to unlock the first rod, the second rod, and the third rod from the plunger requires overcoming a spring force of the third spring by compressing the third spring.

In some embodiments, a first rod is slidably coupled to the outer housing assembly and configured such that moving the first probe proximally (relative to the outer housing assembly) pushes the first rod proximally (relative to the outer housing assembly) to unlock the first rod from the plunger.

In some embodiments, a second rod is slidably coupled to the outer housing assembly and configured to move independently of the first rod such that moving the second probe proximally (relative to the outer housing assembly) pushes the second rod proximally (relative to the outer housing assembly) to unlock the second rod from the plunger.

Some embodiments comprise an injector, which can comprise an outer housing assembly; a syringe coupled at least partially inside the outer housing assembly and having a barrel, a needle, and a plunger; and a first probe slidably coupled to the outer housing assembly and protruding from a distal end of the outer housing assembly. The plunger can be slidably coupled to the barrel such that at least a portion of the plunger is located inside the barrel and such that the plunger is configured to push medicine located inside the barrel out through a needle into a person. The needle can be coupled to a distal end of the barrel. The needle can comprise a lumen located along a central axis of the needle such that the lumen carries medicine from the barrel into the person. A distal end of the plunger can comprise a seal configured to prevent leaking of the medicine. This leak prevention forces the medicine out of the needle when the plunger moves distally relative to the barrel.

In some embodiments, an injector comprises a second probe slidably coupled to the outer housing assembly, protruding from the distal end of the outer housing assembly, and configured to move independently of the first probe. The injector can be configured such that moving both the first probe and the second probe proximally relative to the outer housing assembly unlocks the plunger such that the plunger moves distally relative to the outer housing assembly to inject a medicine through the needle. The injector can be configured such that moving the first probe proximally (relative to the outer housing assembly) without moving the second probe proximally (relative to the outer housing assembly) does not unlock the plunger and such that moving the second probe proximally (relative to the outer housing assembly) without moving the first probe proximally (relative to the outer housing assembly) does not unlock the plunger.

In some embodiments, an injector comprises a first spring located around at least a first portion of the plunger and compressed between a second portion of the outer housing assembly and a radially outward protrusion of the plunger. The injector can be configured such that moving both the first probe and the second probe proximally relative to the outer housing assembly unlocks the plunger such that the first spring moves the plunger distally relative to the outer housing assembly to inject the medicine through the needle into a person.

In some embodiments, an injector comprises a third probe slidably coupled to the outer housing assembly, protruding from the distal end of the outer housing assembly, and configured to move independently of the first probe and the second probe. The first probe, the second probe, and the third probe can form a cylindrical sheath around the needle. The cylindrical sheath can comprise a distal opening configured to enable a distal tip of the needle to exit the distal opening to inject the medicine.

In some embodiments, an injector is configured such that moving the plunger distally relative to the outer housing assembly to inject the medicine requires moving the first probe, the second probe, and the third probe proximally relative to the outer housing assembly.

In some embodiments, the outer housing assembly comprises a first groove and a second groove that are oriented from a distal portion of the outer housing assembly to a first proximal portion of the outer housing assembly. The first probe can comprise a first radially outward protrusion that slidably couples the first probe to the first groove. The second probe can comprise a second radially outward protrusion that slidably couples the second probe to the second groove. The first probe and the second probe can be configured to slide distally and proximally (along grooves) relative to the outer housing assembly.

In some embodiments, the outer housing assembly comprises a third groove and a fourth groove that are oriented from the distal portion of the outer housing assembly to the first proximal portion of the outer housing assembly. The first probe can comprise a third radially outward protrusion that slidably couples the first probe to the third groove. The second probe can comprise a fourth radially outward protrusion that slidably couples the second probe to the fourth groove.

In some embodiments, the first probe comprises a proximally protruding cantilever beam having a second proximal portion that comprises a ramp that protrudes radially outward into a cavity of the outer housing assembly. The injector can be configured such that the ramp impedes a first distal movement of the first probe relative to the outer housing assembly until a second distal movement of the plunger relative to the outer housing assembly causes a force large enough to flex the cantilever beam such that the ramp moves radially inward out of the cavity.

In some embodiments, an injector comprises a first spring located around at least a first portion of the plunger and compressed between a second portion of the outer housing assembly and a fifth radially outward protrusion of the plunger. The injector can be configured such that moving both the first probe and the second probe proximally (relative to the outer housing assembly) unlocks the plunger such that the first spring moves the plunger distally (relative to the outer housing assembly) to cause the force.

In some embodiments, a fifth protrusion is coupled to the first probe by the first radially outward protrusion; a sixth protrusion is coupled to the first probe by the third radially outward protrusion; a seventh protrusion is coupled to the second probe by the second radially outward protrusion; and an eighth protrusion is coupled to the second probe by the fourth radially outward protrusion. The fifth protrusion and the sixth protrusion can protrude toward each other to slidably couple the first probe to the outer housing assembly. The seventh protrusion and the eight protrusion can protrude toward each other to slidably couple the second probe to the outer housing assembly.

In some embodiments, an injector comprises a first rod slidably coupled to the outer housing assembly and configured such that moving the first probe proximally relative to the outer housing assembly unlocks the first rod from the plunger by pushing the first rod proximally relative to the outer housing assembly.

In some embodiments, an injector comprises a second rod slidably coupled to the outer housing assembly and configured such that moving the second probe proximally relative to the outer housing assembly unlocks the second rod from the plunger by pushing the second rod proximally relative to the outer housing assembly.

In some embodiments, an injector comprises a first spring configured to push the plunger distally relative to the outer housing assembly. The injector can be configured such that unlocking the first rod and the second rod from the plunger enables the plunger to move distally relative to the outer housing assembly such that the first spring pushes the plunger distally relative to the outer housing assembly to inject the medicine into a person.

In some embodiments, the outer housing assembly comprises a first groove, a second groove, a third groove, and a fourth groove that are oriented from a distal portion of the outer housing assembly to a proximal portion of the outer housing assembly. The first probe, the second probe, the first rod, and the second rod can be slidably coupled to at least one of the first groove, the second groove, the third groove, and the fourth groove such that the first probe, the second probe, the first rod, and the second rod can move proximally relative to the outer housing assembly by sliding along tracks of the first groove, the second groove, the third groove, and the fourth groove.

In some embodiments, the outer housing assembly comprises a central axis from the distal portion of the outer housing assembly to the proximal portion of the outer housing assembly. The first groove, the second groove, the third groove, and the fourth groove can be oriented within ten degrees of parallel to the central axis and/or within twenty degrees of parallel to the central axis.

In some embodiments, the first probe comprises a first L-shaped protrusion and a second L-shaped protrusion that slidably couple the first probe to at least one of the first groove, the second groove, the third groove, and the fourth groove.

In some embodiments, the first rod comprises a first T-shaped protrusion that slidably couples the first rod to at least one of the first groove, the second groove, the third groove, and the fourth groove.

In some embodiments, an injector comprises a second spring located around at least a first portion of the plunger and compressed between a first radially outward protrusion of the plunger and at least one of the first probe and the second probe. The second spring can be configured to push the first probe and the second probe distally relative to the outer housing assembly to cause the first probe and the second probe to move distally relative to the outer housing assembly to hide the needle after the needle has injected the medicine. Hiding the needle can prevent needlestick injuries.

In some embodiments, an injector comprises a third spring compressed between a proximal end of the outer housing assembly and a second portion of the first rod such that the third spring is configured to push the first rod and the second rod distally relative to the outer housing assembly. The injector can be configured such that moving the first probe and the second probe proximally relative to the outer housing assembly to push the first rod and the second rod proximally (relative to the outer housing assembly) to unlock the first rod and the second rod from the plunger requires overcoming a spring force of the third spring.

In some embodiments, the first spring has a first spring constant that is at least twice a second spring constant of the second spring. In some embodiments, the first spring has a first spring constant that is at least twice a third spring constant of the third spring and/or at least three times the third spring constant of the third spring. In some embodiments, the second spring has a second spring constant that is at least twice a third spring constant of the third spring. The relatively high first spring constant of the first spring relative to the second spring and the third spring enables the first spring to dominate the second spring and the third spring. This way, the first spring can overpower the second spring such that the strong force of the first spring enables the first spring to compress the second spring. The relatively low spring constant of the third spring makes it relatively easy to move the first probe and the second probe proximally relative to the outer housing assembly and thereby push the first rod and the second rod proximally to unlock the first rod and the second rod from the plunger to enable the first spring to drive the plunger distally (relative to the outer housing assembly) to inject the medicine.

In some embodiments, an injector comprises a third probe slidably coupled to the outer housing assembly. The injector can be configured such that after the medicine is injected, the first probe, the second probe, and the third probe move distally relative to the outer housing assembly to form a cylindrical sheath that blocks a distal end of the needle from needlestick punctures. The cylindrical sheath can protect people administering injections from needlestick punctures.

In some embodiments, the first probe, the second probe, and the third probe are spaced radially outward around a perimeter of the needle.

In some embodiments, a first rod comprises a first radially inward protrusion and the second rod comprises a second radially inward protrusion. The first radially inward protrusion and the second radially inward protrusion can lock the plunger relative to the outer housing assembly such that the plunger cannot move distally relative to the outer housing assembly.

In some embodiments, the first rod and the second rod are at least 30 millimeters long as measured along a central axis of the outer housing assembly.

In some embodiments, the first probe comprises a proximally facing end that abuts a distally facing end of the first rod, and the injector is configured such that the proximally facing end pushes the distally facing end proximally.

In some embodiments, the outer housing assembly is configured to limit a maximum distal movement of the first rod such that the first probe is configured to continue moving distally after the outer housing assembly prevents further distal movement of the first rod.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIG. 24 illustrates a perspective view of a rod, according to some embodiments.

FIG. 25 illustrates a side view of the rod, according to some embodiments.

FIG. 26 illustrates a perspective view of the rod, according to some embodiments.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Injectors can be used to inject medicine into a person. Injectors can inject many different types of medicines.

Some injectors inject epinephrine into people suffering a severe, potentially life-threatening allergic reaction called anaphylaxis. People suffering from anaphylaxis need an injection of epinephrine immediately and often cannot wait for an ambulance or wait to arrive at a hospital to receive an injection of epinephrine. As a result, epinephrine injections are commonly administered by a person without medical training. Often, people experiencing anaphylactic shock have to inject themselves with epinephrine. Failing to administer the injection correctly, however, can have life-threatening consequences. Unfortunately, incorrect administration of epinephrine injections is far too common.

Many embodiments described herein dramatically reduce the odds of incorrect administration of injections of medications. Many embodiments are particularly well suited to emergency situations where panic and lack of training combine to severely jeopardize injection procedures.

One key failure mode of these injections is failing to insert the needle into the patient while the medicine is propelled from the injector. This error results in the medicine not entering the patient's body. As a result, the medicine cannot save the patient's life.

Figure 1:
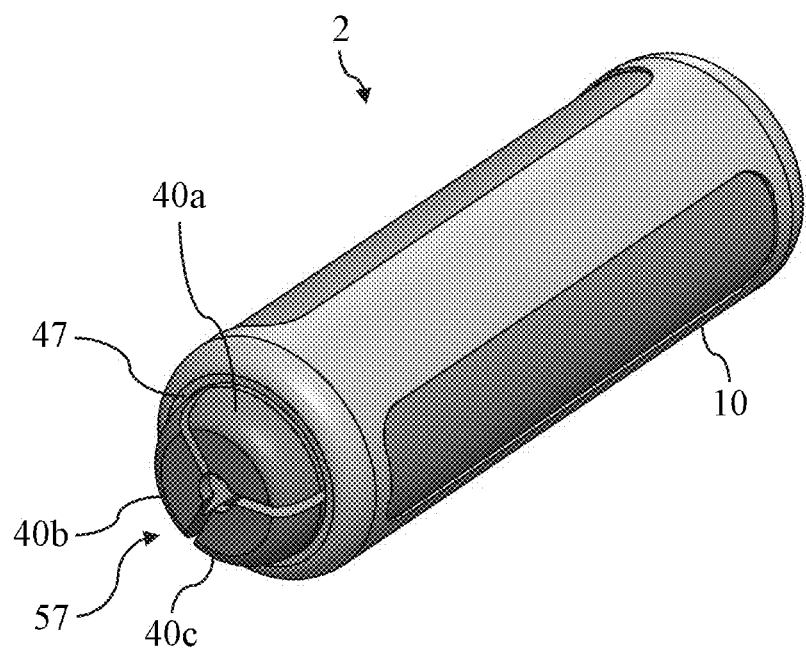
FIGS. 1 and 2 illustrate perspective views of an injector, according to some embodiments.
Figure 2:
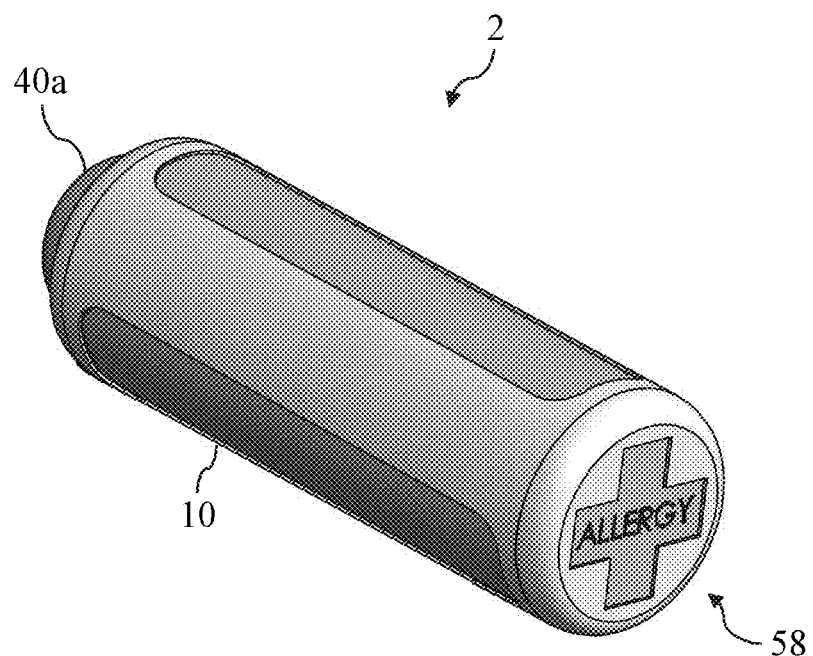
Figure 3A:
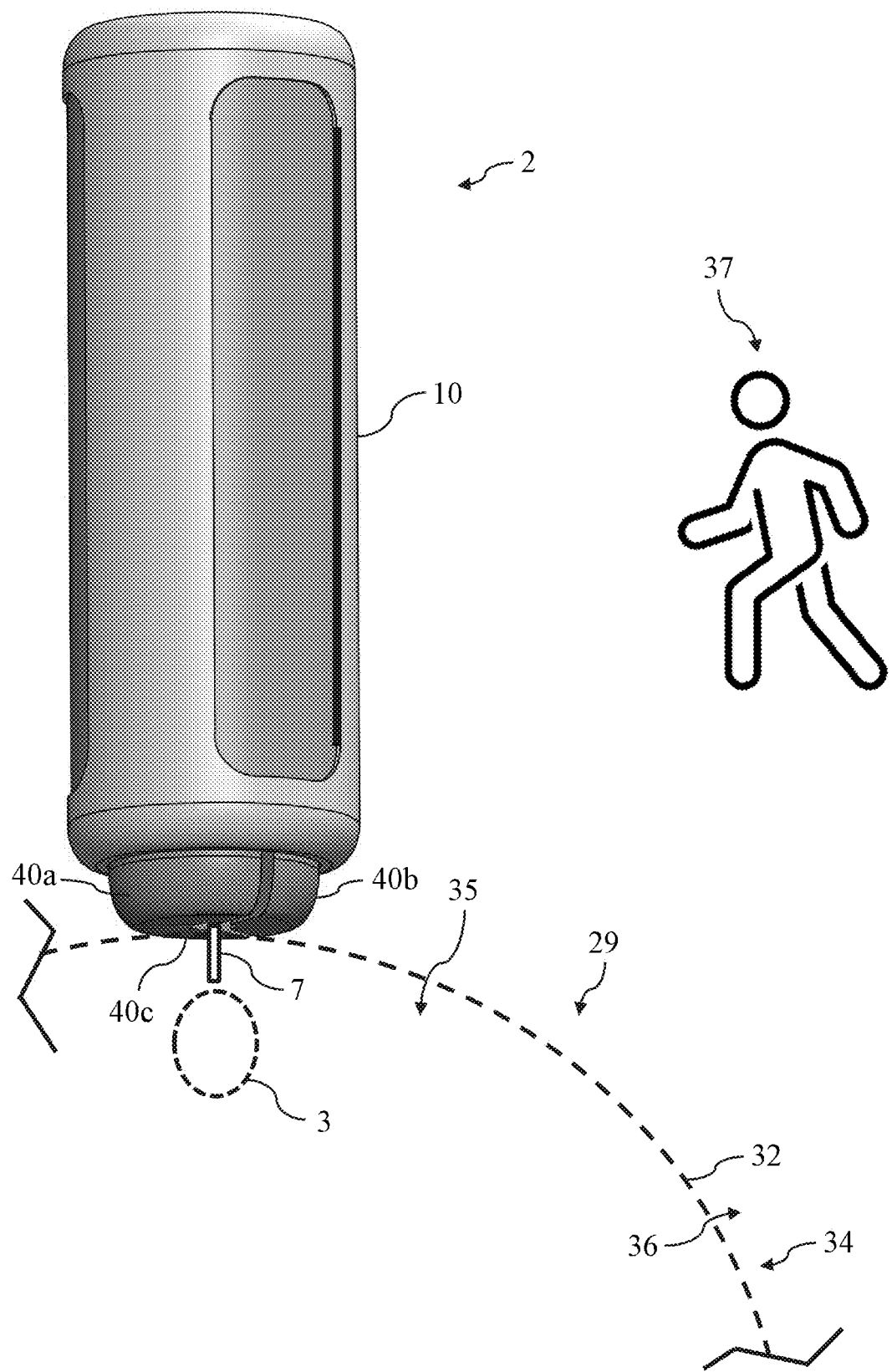
FIG. 3A illustrates a perspective view of the injector, according to some embodiments.
Figure 3B:
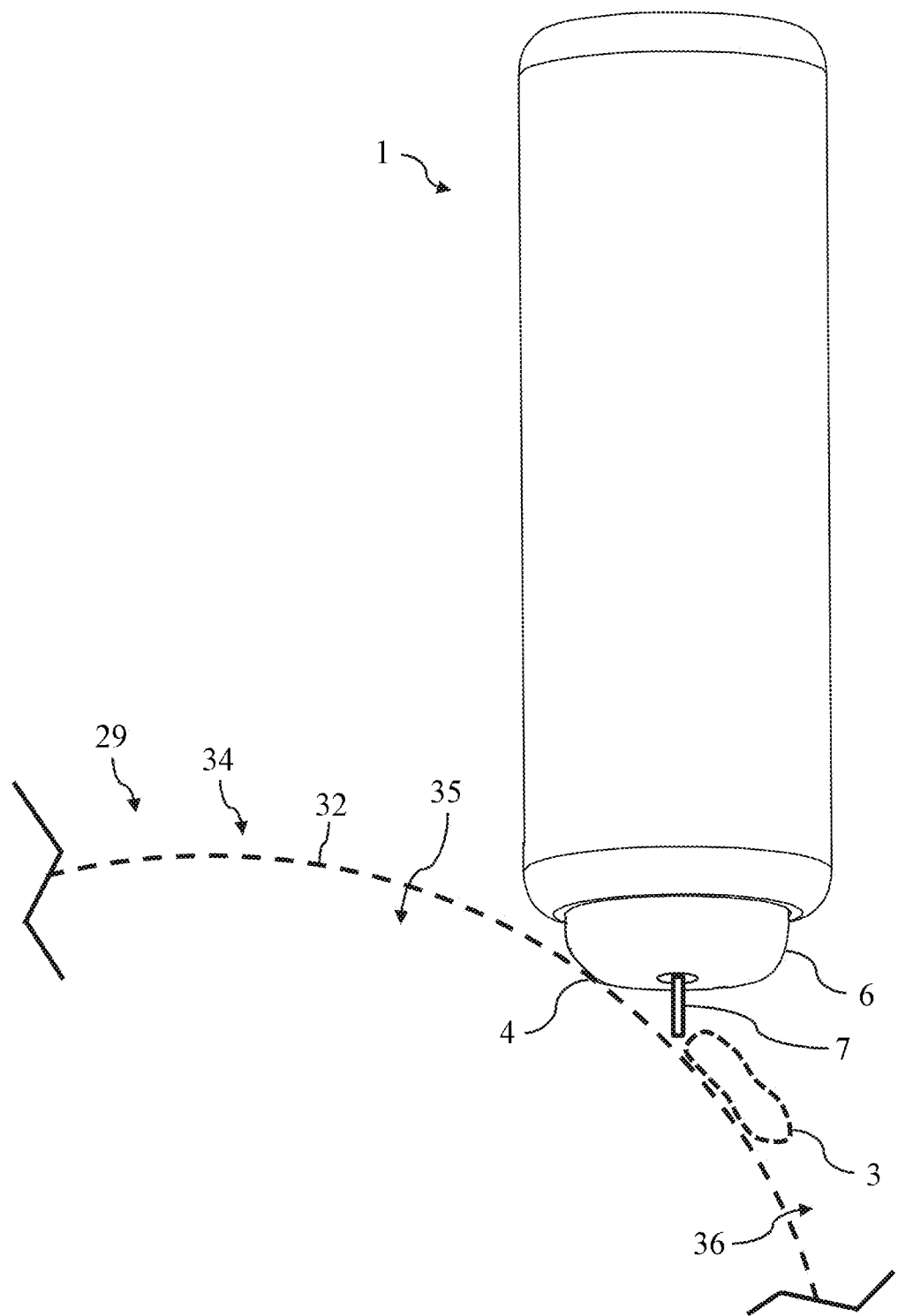
FIG. 3B illustrates a perspective view of an injector, according to some embodiments.
Figure 3C:
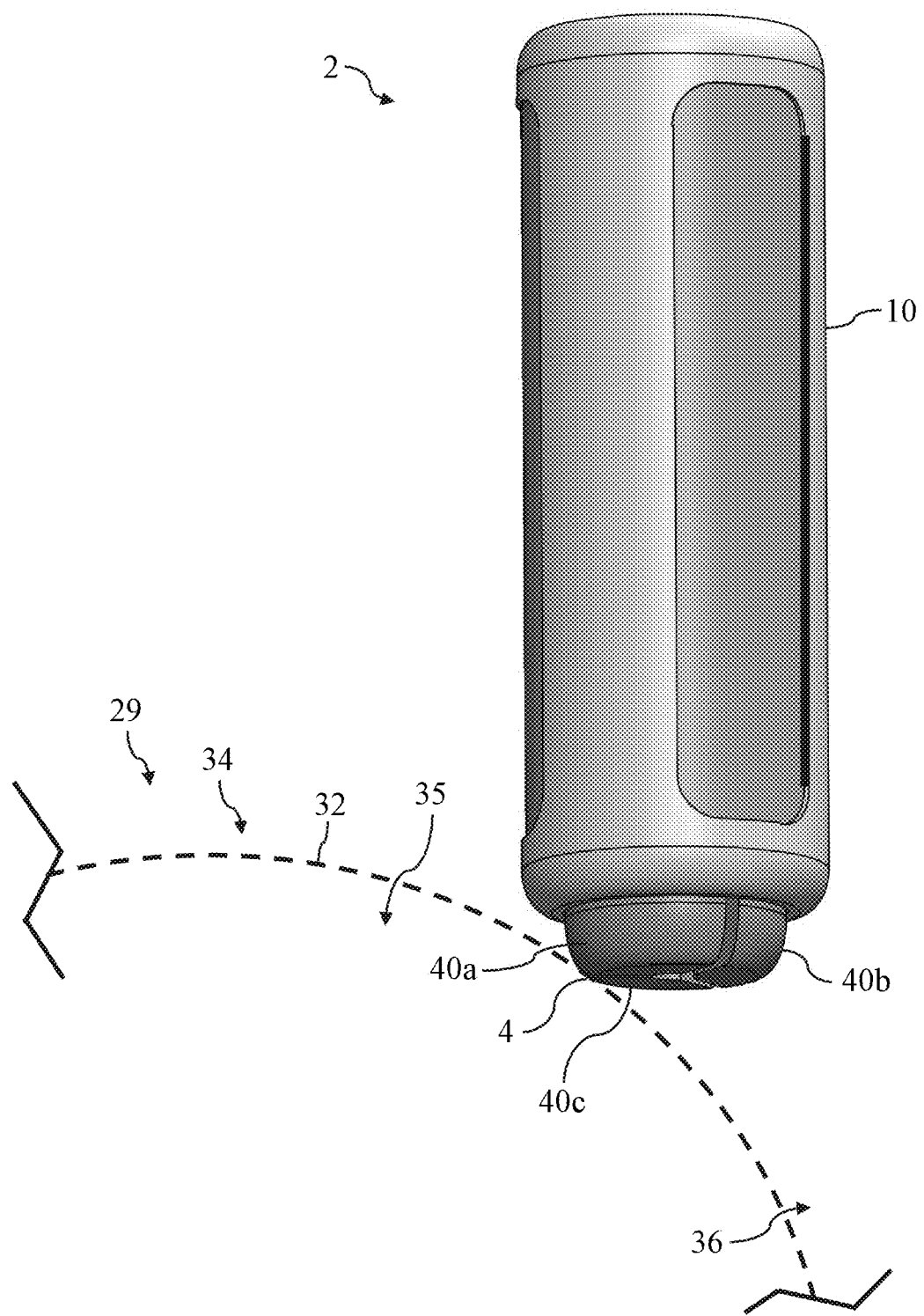
FIG. 3C illustrates a perspective view of the injector illustrated in FIG. 1, according to some embodiments.

Referring now primarily to FIGS. 3A, 3B, and 3C, imagine that a first panicked person 37 without any medical training is trying to inject medicine 3 into a second person 29 in anaphylactic shock. The first panicked person 37 is not sure how to inject the medicine 3 and cannot see the anaphylactic person's leg 34 due to baggy jeans that the anaphylactic person 29 is wearing. The first panicked person 37 swings an injector 2, 1 toward the leg 34 while the anaphylactic person 29 (often a child) squirms trying to avoid the needle 7.

In FIG. 3A, the first panicked person 37 swings a distal end 57 of the injector 2 into the second person's leg 34. Luckily, the swing is a direct hit and the needle 7 moves distally relative to the outer housing assembly 10 of the injector 2 such that the needle 7 moves deeply into the second person's leg 34 to correctly deliver the medicine 3. Now that the medicine 3 is inside 35 the second person 29, the medicine 3 can save the second person's life.

FIG. 3B, however, illustrates a critical failure. In FIG. 3B, the first panicked person 37 swings a distal end of an injector 1 into the second person's leg 34. However, the swing is not a direct hit, which causes the needle 7 and the medicine 3 to be deployed outside 36 of the second person's body. As a result, the medicine 3 is not delivered into the second person 29. The medicine 3 cannot save the second person's life.

To protect against the situation explained in FIG. 3B, some injector manufacturers use triggering mechanisms that protrude from a distal end of an outer housing assembly. These mechanisms, however, have a critical shortcoming that is overcome by many embodiments described herein. The critical shortcoming is that the trigger 6 is placed on the distal end of the injector 1 such that if any portion of the trigger 6 is pressed against the second person 29, the needle 7 will release the medicine 3. As shown in FIG. 3B, a portion 4 of the trigger 6 can be pressed against the second person's skin 32 and thus could cause the release of the medicine 3 even if the injector 1 is not positioned to actually place the needle 7 inside 35 of the body of the second person 29. Thus, there is a need for systems and methods that preclude release of the medicine 3 unless an injector is positioned to place the needle 7 inside 35 the body of the person 29 who needs the medicine 3.

FIG. 3C shows the situation illustrated in FIG. 3B except that the injector 2 includes innovative mechanisms that prevent release of the medicine 3 even though the portion 4 of the trigger is pressed against the second person's skin 32. As a result, the first person 37 can try as many times as necessary to properly inject the medicine 3 rather than being limited to a single attempt to inject the medicine 3.

Thus, many embodiments described herein can save lives by ensuring that people receive their life-saving medicine 3 rather than being left without any way to receive their medicine 3 due to using an injector 2 that releases the medicine 3 even though the injector 2 is not properly positioned.

Figure 5:
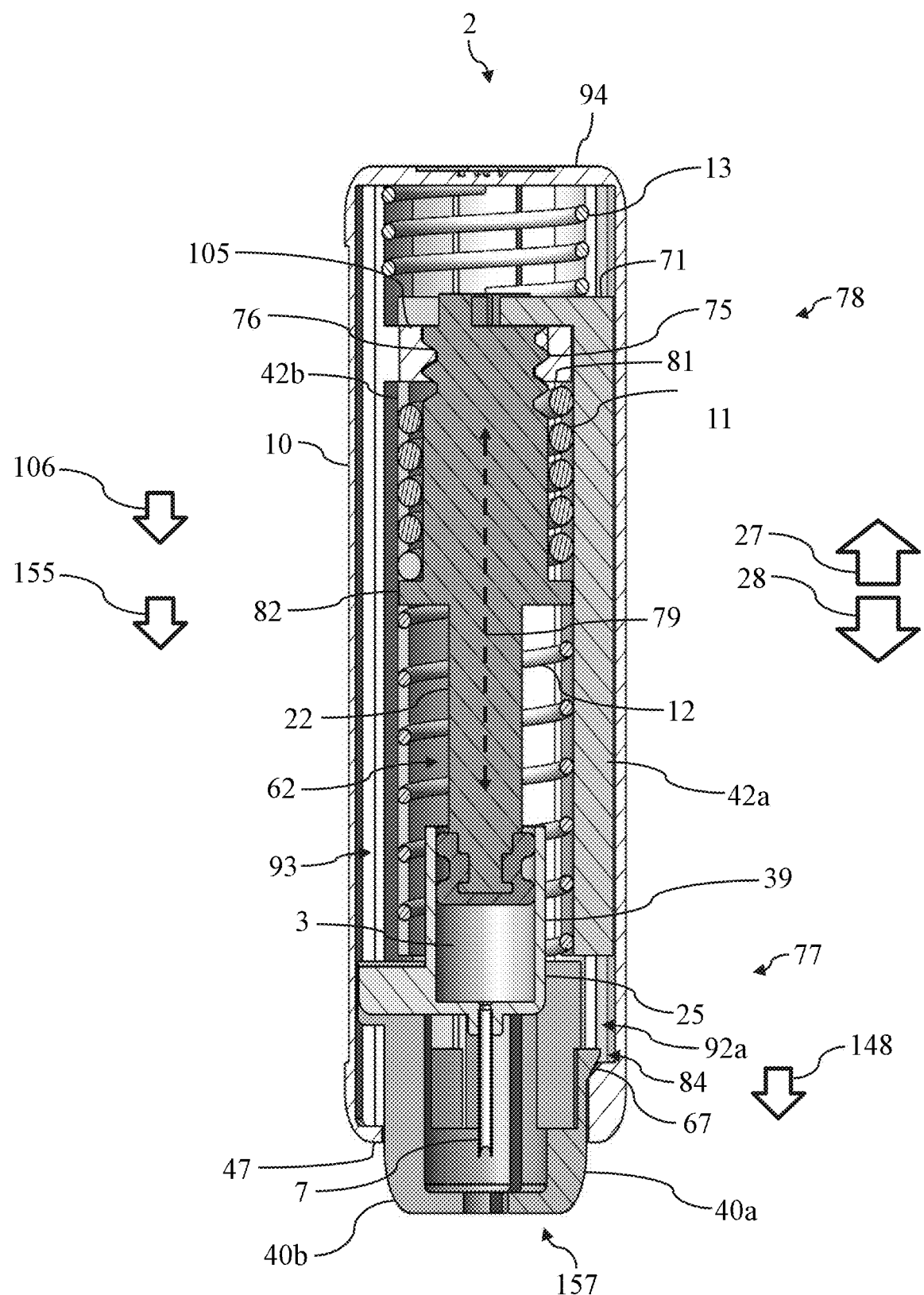
FIG. 5 illustrates a cross-sectional view of the injector taken along line 5 in FIG. 4, according to some embodiments.

FIGS. 5, 14, 16, 17, and 18 illustrate five states of the injector 2. Referring now primarily to FIG. 5, in many embodiments a first spring 11 has a much larger spring constant than a second spring 12 and a third spring 13. Once released, the first spring 11 pushes the plunger 22 distally relative to the outer housing assembly 10. Due to the relatively incompressible nature of the medicine 3, moving the plunger 22 distally moves the barrel 25 and needle 7 of the syringe 39 distally (relative to the outer housing assembly 10) such that the needle 7 enters a person 29. The first spring 11 continues to push the plunger 22 distally, which forces the medicine 3 out of the needle 7 and into the person 29.

In some embodiments, the outer housing assembly 10 comprises multiple molded pieces that are assembled together. In some embodiments, the outer housing assembly 10 comprises a single molded part.

In some embodiments, the plunger 22 is threadably coupled to the outer housing assembly 10 such that the plunger 22 must rotate relative to the outer housing assembly 10 in order for the plunger 22 to move distally relative to the outer housing assembly 10. The first spring 11 provides more than enough force to rotate the plunger 22 relative to the outer housing assembly 10 except for the fact that in some embodiments, rods 42a, 42b, 42c rotationally lock the plunger 22 such that the plunger 22 cannot rotate relative to the outer housing assembly 10 (until the rods 42a, 42b, 42c are unlocked).

Figure 6:
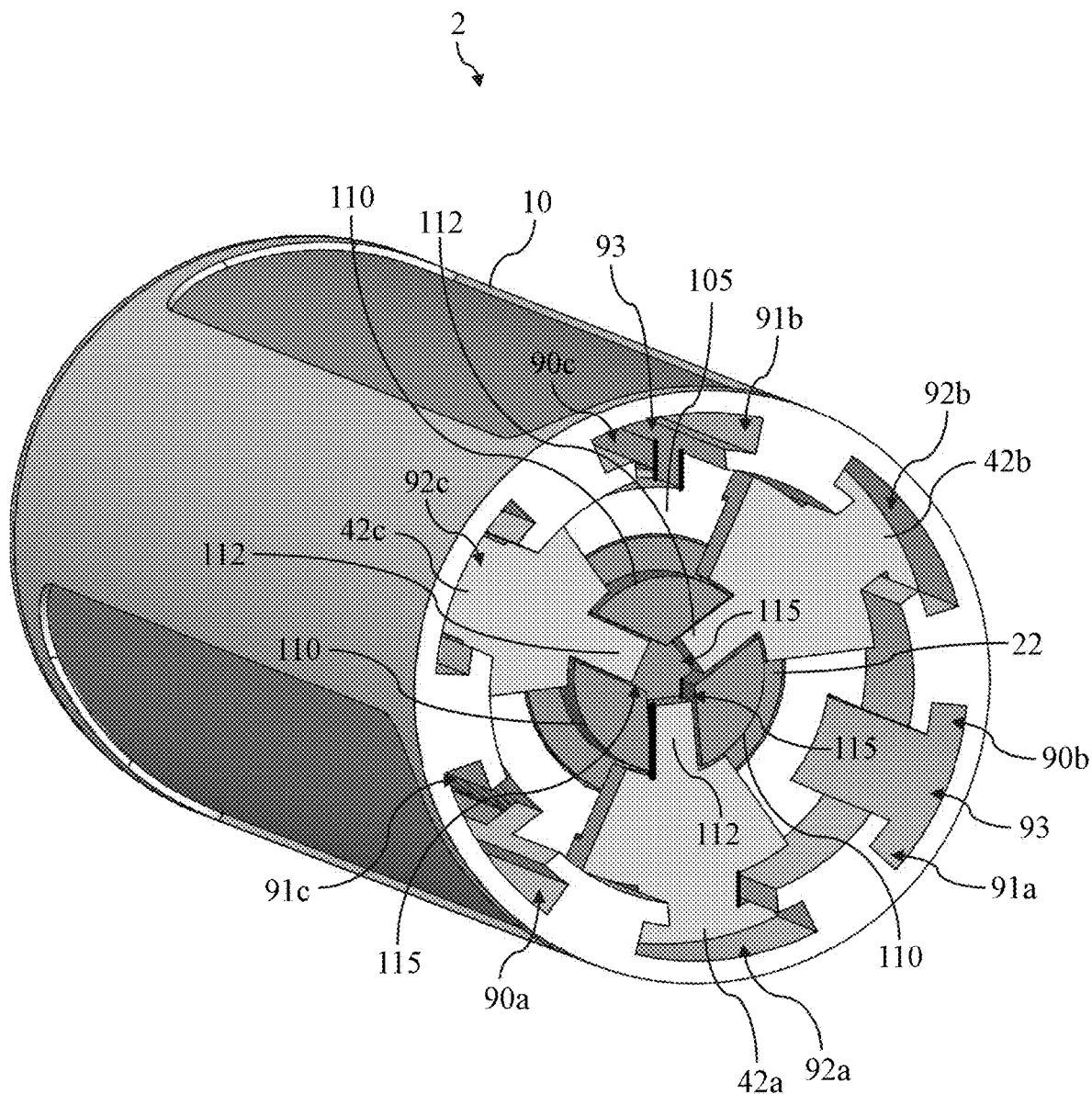
FIG. 6 illustrates a perspective view of the injector with a proximal portion of the outer housing hidden, according to some embodiments.
Figure 7:
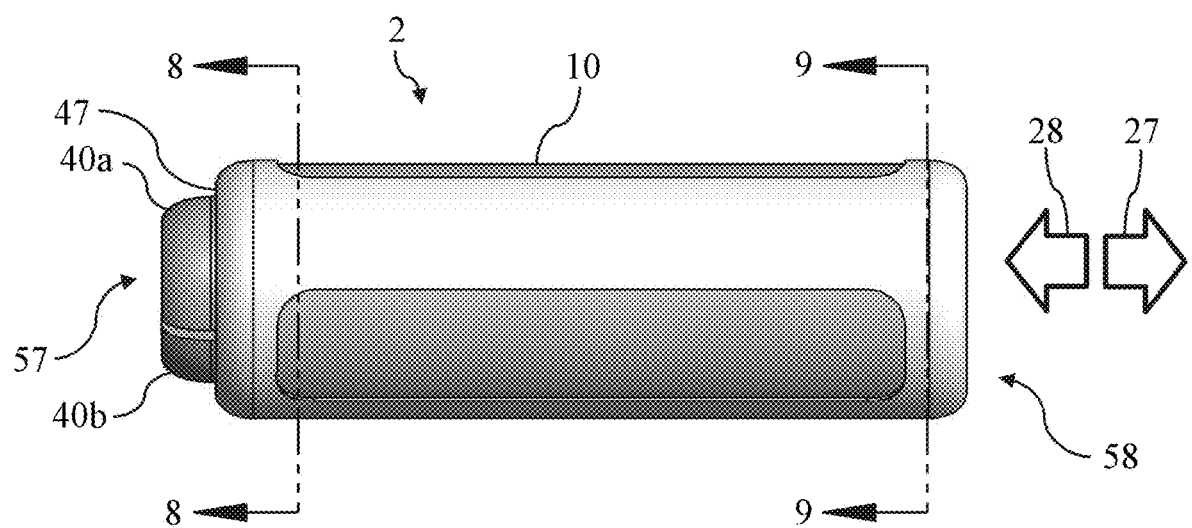
FIG. 7 illustrates a side view of the injector, according to some embodiments.
Figure 12:
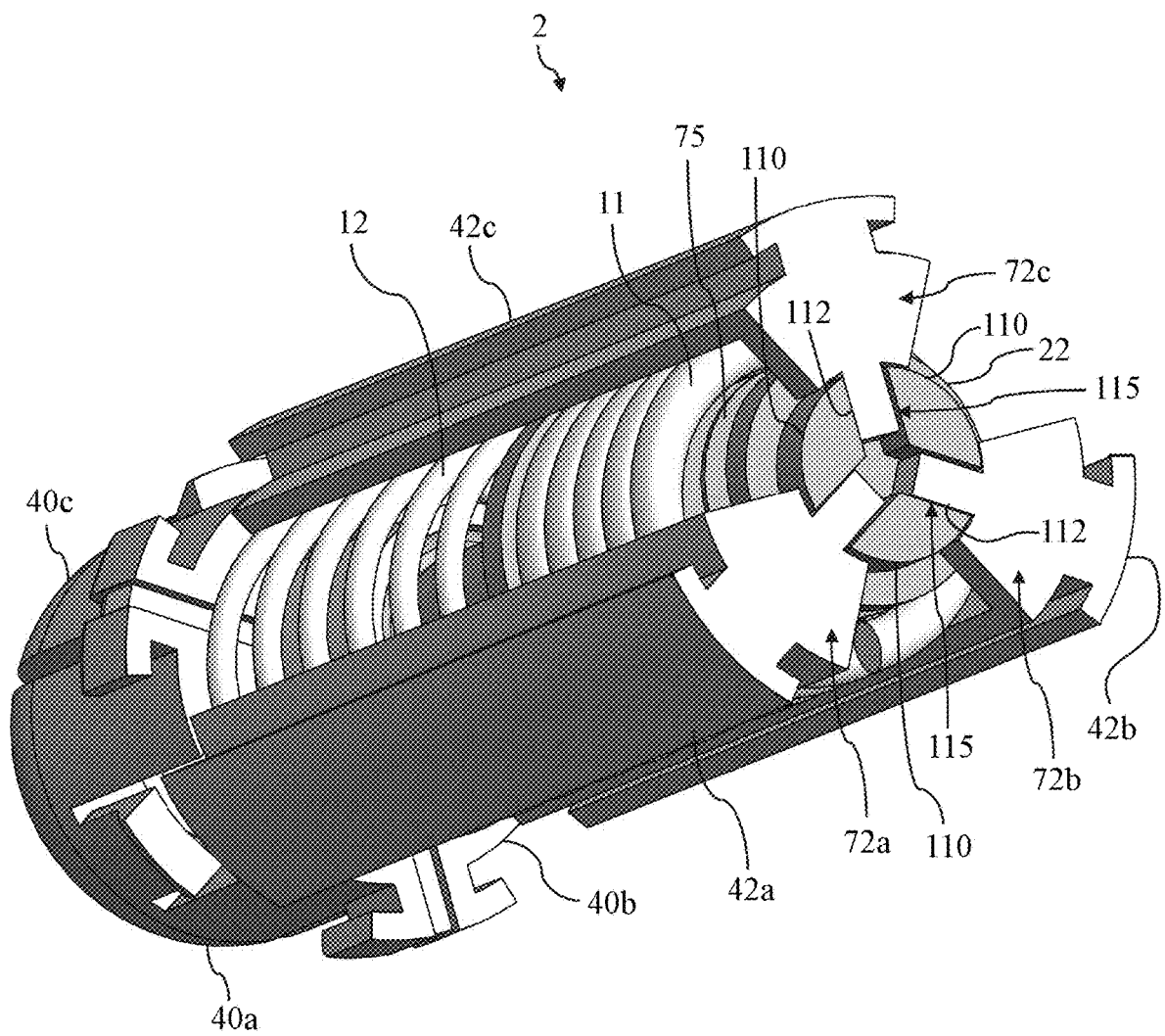
FIG. 12 illustrates a perspective view of the injector with an outer housing assembly and a spring hidden, according to some embodiments.

As shown in FIGS. 6 and 12, a proximal portion 70 of the plunger 22 can comprise protrusions 110 that form channels 115. Inward protrusions 112 of the rods 42a, 42b, 42c can reside at least partially in the channels 115 of the plunger 22 such that the rods 42a, 42b, 42c must be moved proximally (relative to the outer housing assembly 10 and/or relative to the protrusions 110) to move the inward protrusions 112 out of the channels 115 to unlock the plunger 22 such that the plunger 22 can rotate relative to the outer housing assembly 10.

Figure 13:
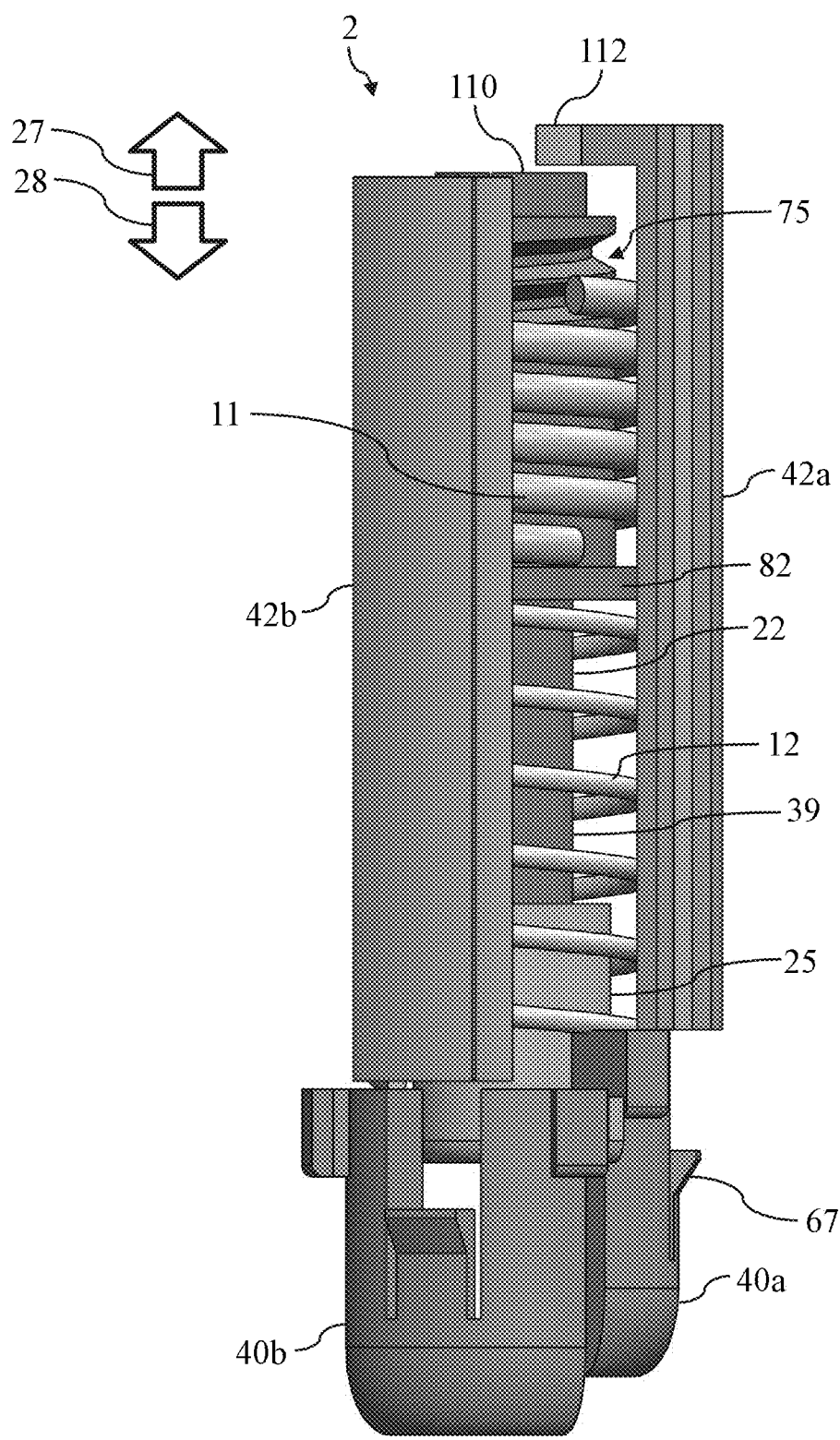
FIG. 13 illustrates a side view of the injector with an outer housing assembly and a spring hidden, according to some embodiments.

FIG. 13 illustrates that one of the rods 42a was moved proximally such that the inward protrusion 112 of the rod 42a no longer resides in the channel 115 of the plunger 22 such that the rod 42a no longer locks the plunger 22. Thus, this rod 42a does not prevent rotational movement of the plunger 22 relative to the outer housing assembly 10.

However, another rod 42b shown in FIG. 13 has not been moved proximally. Thus, this rod 42b has an inward protrusion 112 that resides in the channel 115 of the plunger 22 such that the rod 42b locks the plunger 22 and prevents rotational movement of the plunger 22 relative to the outer housing assembly 10. Therefore, even though one rod 42a was moved proximally, another rod 42b still prevents the needle 7 and medicine 3 from being deployed.

In some embodiments, moving the rods proximally relative to the outer housing assembly 10 requires moving all the probes proximally relative to the outer housing assembly 10, which requires pressing all the probes against the person 29 receiving the injection. If only some of the probes are pressed against the person 29, then some of the rods will remain locked, which prevents the plunger 22 from being unlocked, which prevents deployment of the needle 7 and medicine 3. Thus, many embodiments can preclude needle 7 and medicine 3 deployment if the injector 2 is not positioned correctly.

FIG. 5 illustrates a third spring 13 that is compressed such that the third spring 13 prevents the rods 42*a*, 42*b*, 42*c* from moving proximally relative to the outer housing assembly 10 under the force of gravity. The third spring 13 prevents the rods 42*a*, 42*b*, 42*c* from inadvertently moving proximally when, for example, a person 37, 29 holds the injector 2 upside down.

Figure 14:
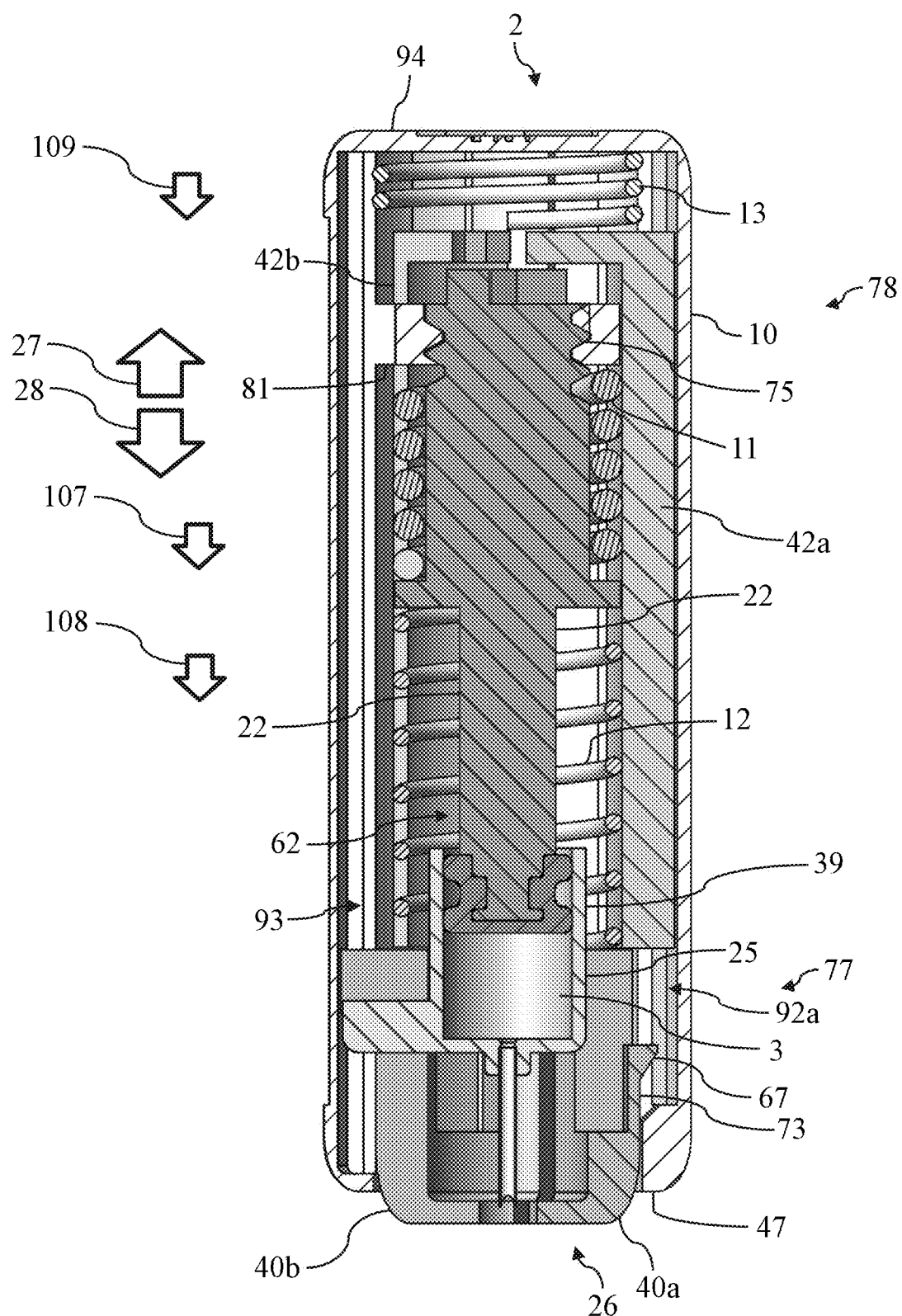
FIG. 14 illustrates a cross-sectional view of the injector taken along line 5 in FIG. 4, according to some embodiments.

FIG. 14 illustrates a state in which all three rods 42*a*, 42*b*, 42*c* have been moved proximally (relative to the outer housing assembly 10) such that the inward protrusions 112 of the rods 42*a*, 42*b*, 42*c* no longer reside in the channels 115 of the plunger 22. Thus, the plunger 22 is unlocked and the first spring 11 can push the plunger 22 such that the plunger 22 can rotate relative to the outer housing assembly 10 and can move distally relative to the outer housing assembly 10.

In some embodiments, the plunger 22 can move distally relative to the outer housing assembly 10 without rotating once the rods 42*a*, 42*b*, 42*c* are unlocked.

Note the positions of the probes 40*a*, 40*b* 40*c* in FIG. 14 compared to the positions of the probes 40*a*, 40*b* 40*c* in FIG. 5. In FIG. 14, all the probes 40*a*, 40*b* 40*c* have been pressed against a person's skin 32 (directly or indirectly through clothing) such that all the probes 40*a*, 40*b* 40*c* have moved proximally relative to the outer housing assembly 10. This proximal movement 123 of the probes 40*a*, 40*b* 40*c* has pushed the rods 42*a*, 42*b*, 42*c* proximally to unlock the rods 42*a*, 42*b*, 42*c* from the plunger 22.

Figure 15:
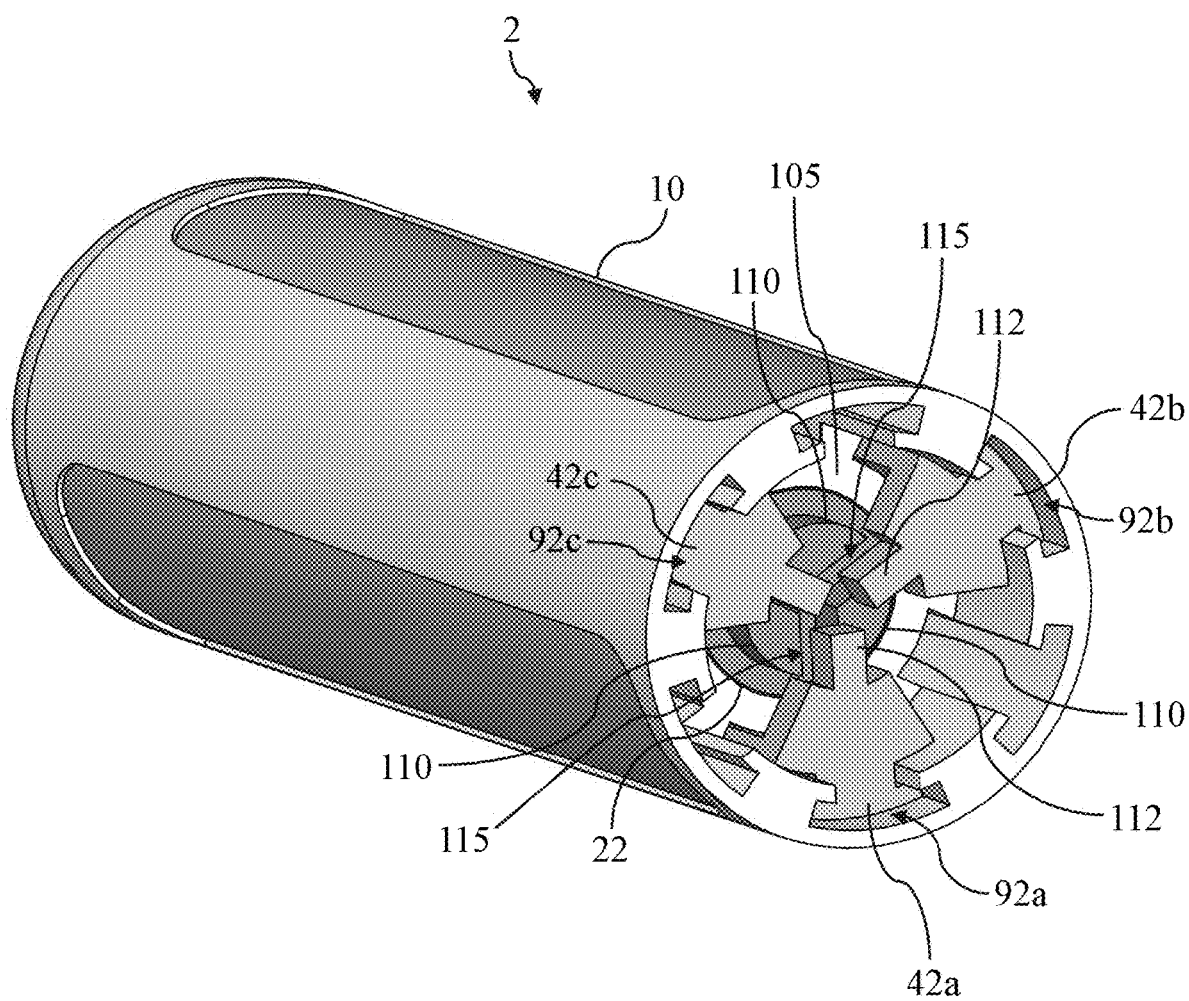
FIG. 15 illustrates a perspective view of the injector with a proximal portion of the outer housing hidden, according to some embodiments.

FIG. 15 illustrates that the inward protrusions 112 of the rods 42*a*, 42*b*, 42*c* are located proximally of the channels 115 of the plunger 22 such that the inward protrusions 112 of the rods 42*a*, 42*b*, 42*c* are not located in the channels 115 of the plunger 22.

FIG. 14 illustrates that the third spring 13 has been compressed relative to the state of the third spring 13 illustrated in FIG. 5. Thus, in some embodiments, moving the rods 42*a*, 42*b*, 42*c* proximally relative to the outer housing assembly 10 requires compressing the third spring 13.

Figure 16:
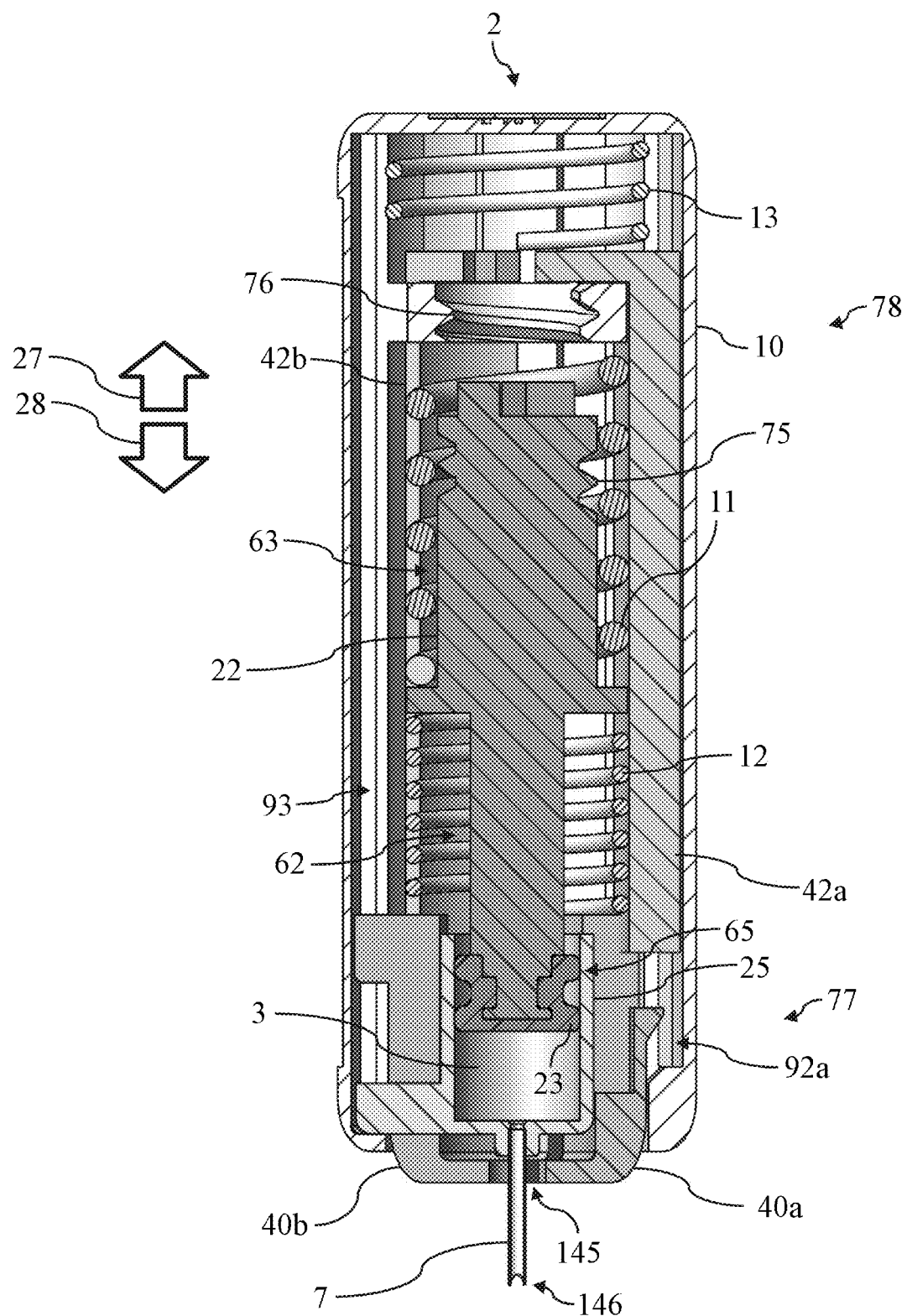
FIGS. 16 to 18 illustrate cross-sectional views of the injector taken along line 5 in FIG. 4, according to some embodiments.

FIG. 16 illustrates a state in which the first spring 11 has pushed the plunger 22 distally such that the plunger 22 has moved the needle 7 distally relative to the outer housing assembly 10 such that the needle 7 has exited a hole between the probes 40*a*, 40*b*, 40*c*. Then, the first spring 11 continues to push the plunger 22 distally relative to the outer housing assembly 10, which forces the medicine 3 to exit a lumen 51 in the needle 7.

Figure 17:
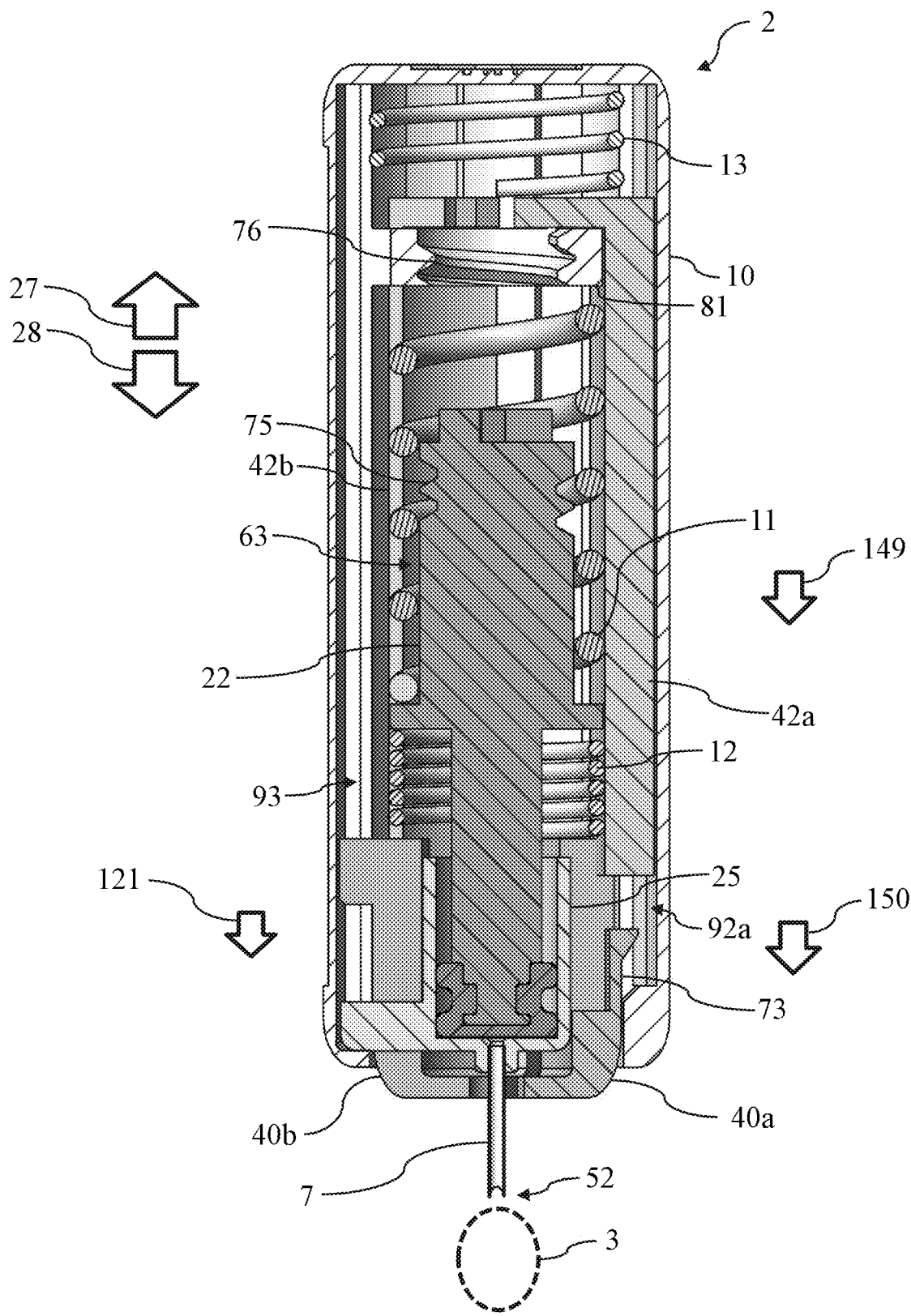
Figure 18:
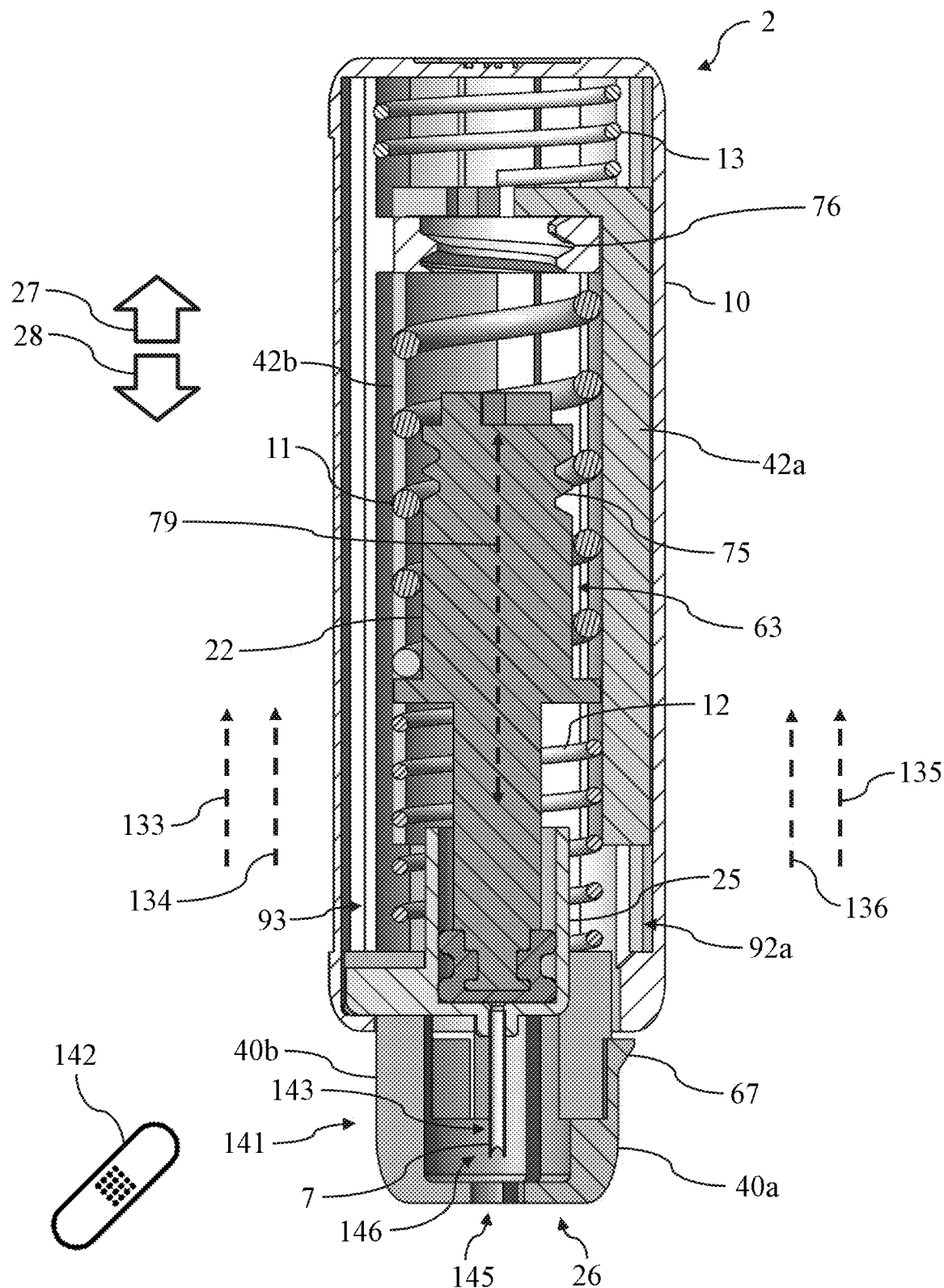

FIG. 17 illustrates a state immediately after plunger 22 has pushed the medicine 3 out of the needle 7. Note that a second spring 12 is compressed between plunger 22 and the probes 40*a*, 40*b*, 40*c*. Note that the second spring 12 is more compressed in FIG. 16 than in FIG. 14. Note that the second spring 12 is more compressed in FIG. 17 than in FIG. 16. Once the plunger 22 is unlocked, the first spring 11 expands, which causes the second spring 12 to compress. (The first spring 11 can have a spring constant that is much larger than a spring constant of the second spring 12 to enable the first spring 11 to dominate the second spring 12.)

This compression of the second spring 12 creates a spring force 108 in the second spring 12 that moves the probes 40*a*, 40*b*, 40*c* distally relative to the outer housing assembly 10 such that the probes 40*a*, 40*b*, 40*c* form a cylindrical sheath 141 around the deployed needle 7 to prevent needlestick injuries. Each probe 40*a*, 40*b*, 40*c* can include a cantilever beam 73 flex arm configured to prevent inadvertent distal deployment of the probes 40*a*, 40*b*, 40*c*. However, the compression of the second spring 12 creates a spring force 108 that is sufficient to cause the cantilever beam 73 flex arm to flex radially inward (relative to the outer housing assembly 10) to unlock the flex arm from the outer housing assembly 10 such that the probe can move distally relative to the outer housing assembly 10 to create a sheath 141 around the deployed needle 7 to prevent needlesticks.

Figure 19:
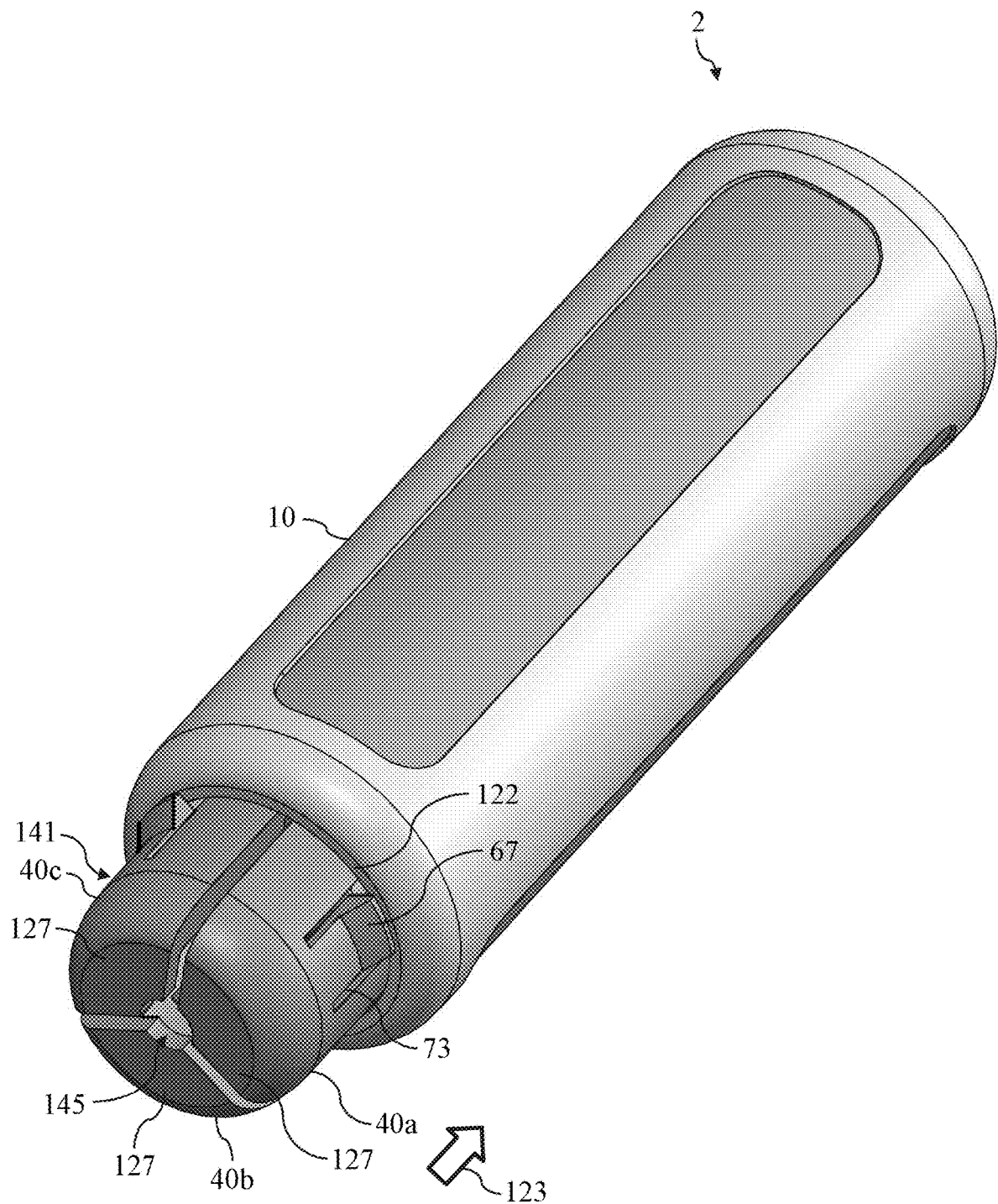
FIG. 19 illustrates a perspective view of the injector, according to some embodiments.
Figure 20:
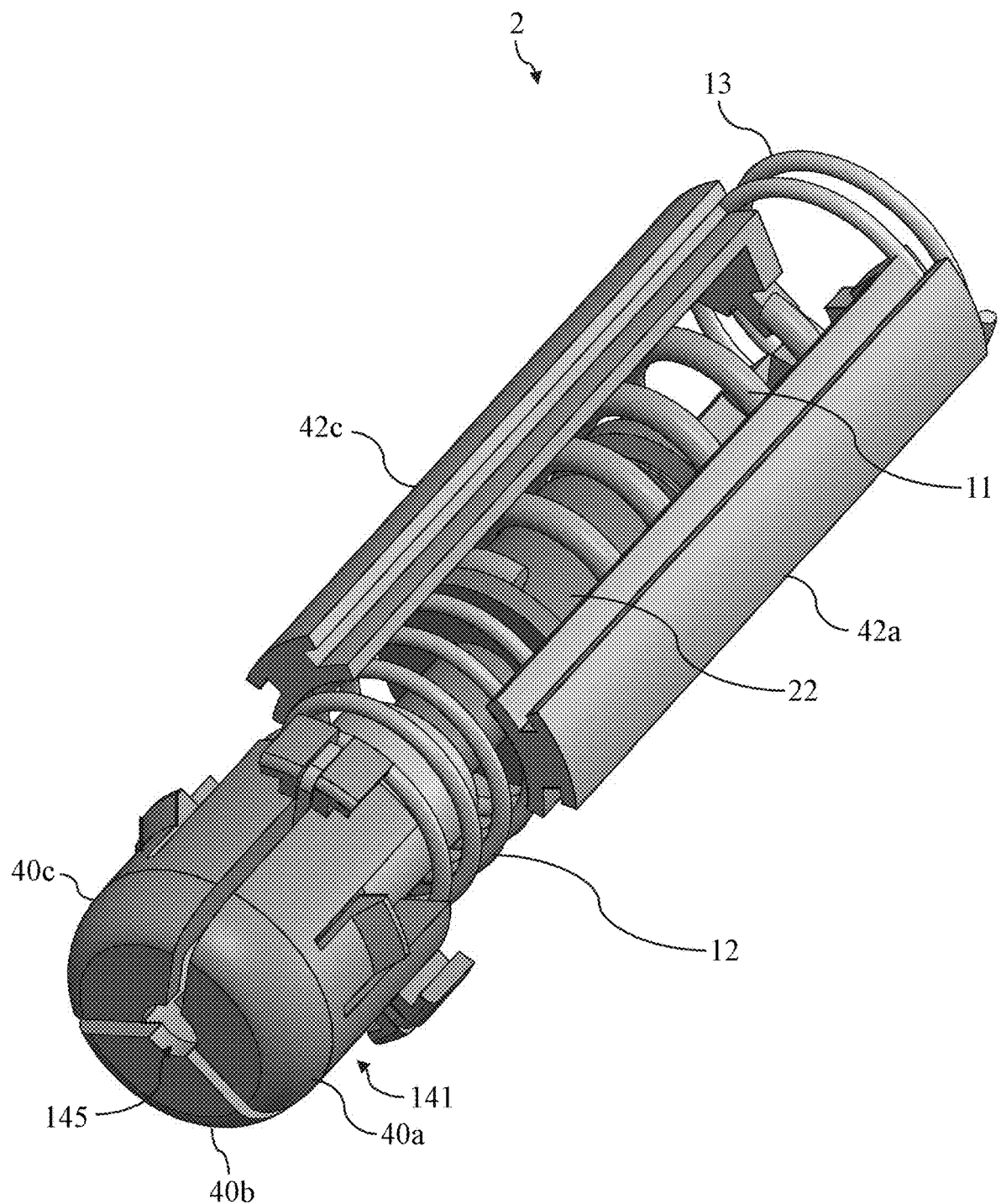
FIG. 20 illustrates a perspective view of the injector with an outer housing assembly hidden, according to some embodiments.
Figure 21:
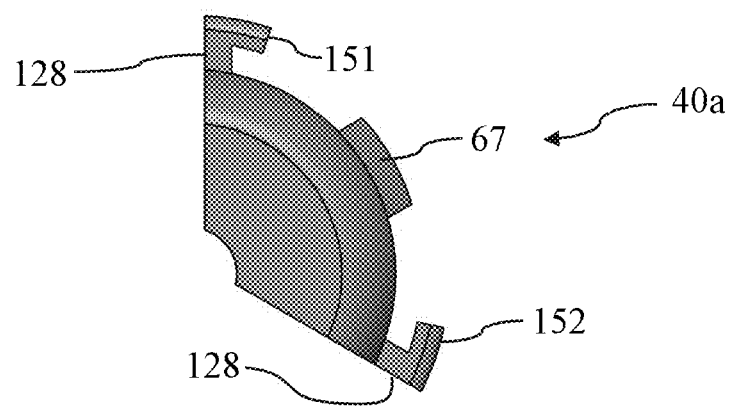
FIG. 21 illustrates a bottom view of a probe, according to some embodiments.
Figure 22:
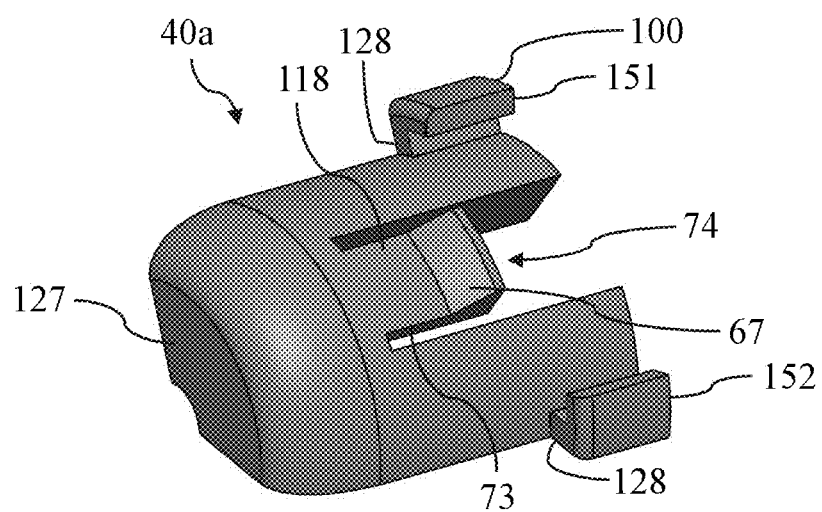
FIGS. 22 and 23 illustrate perspective views of the probe, according to some embodiments.
Figure 23:
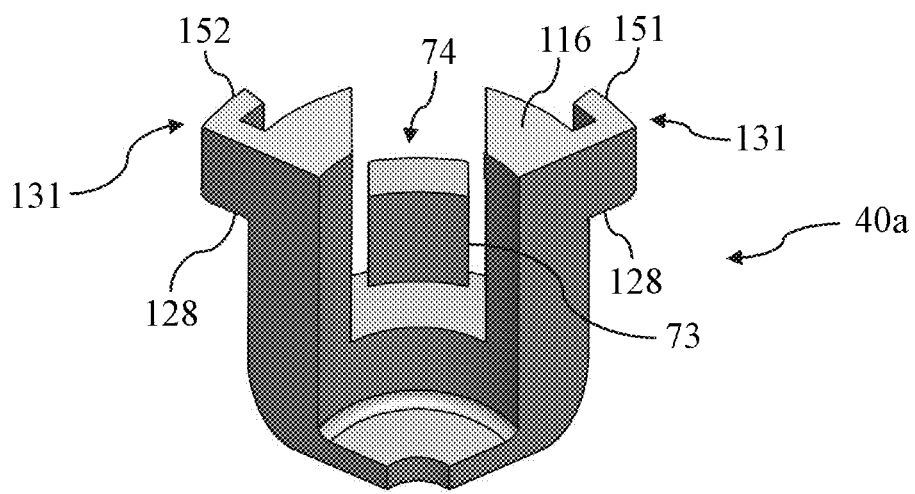
Figure 27:
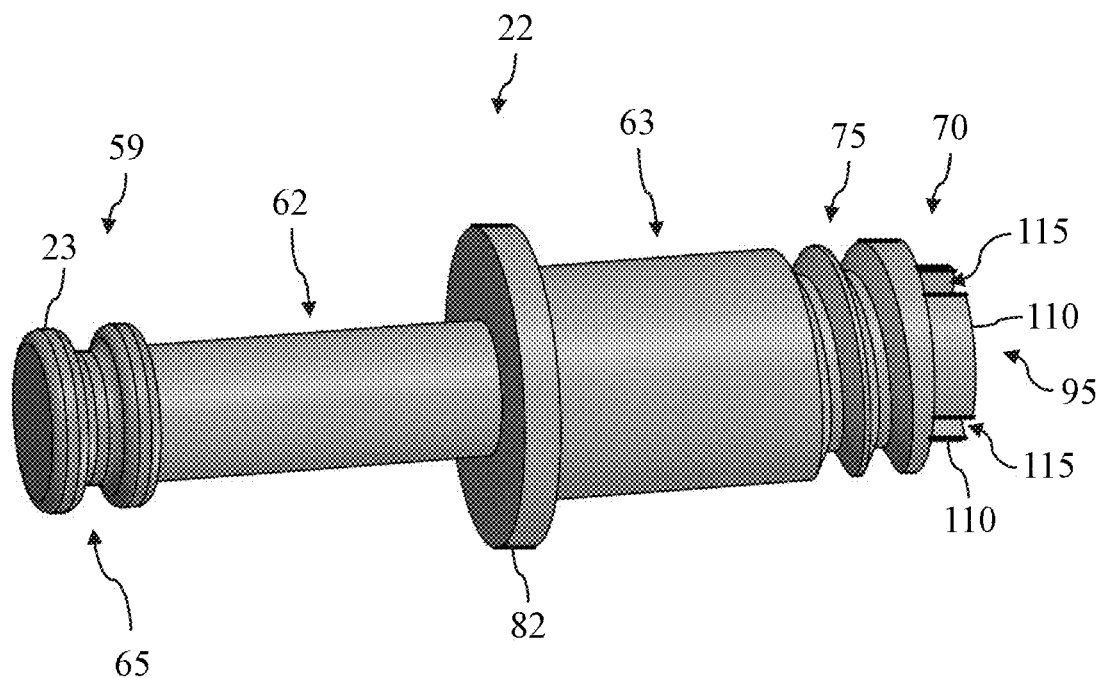
FIGS. 27 and 28 illustrate perspective views of a plunger, according to some embodiments.
Figure 28:
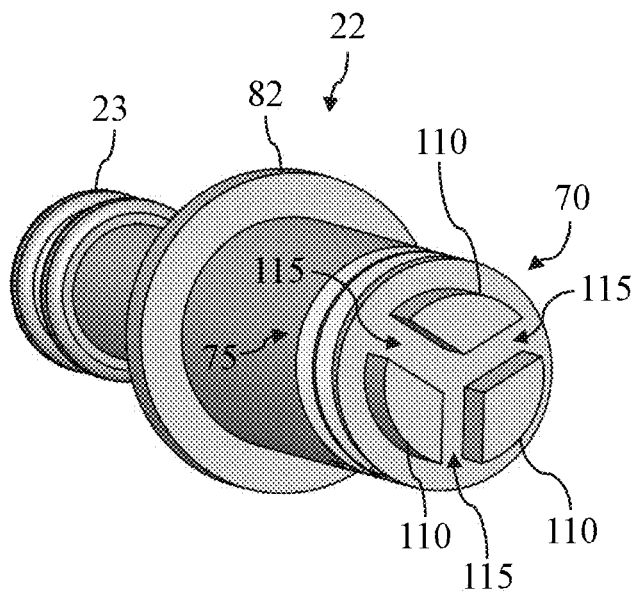
Figure 29:
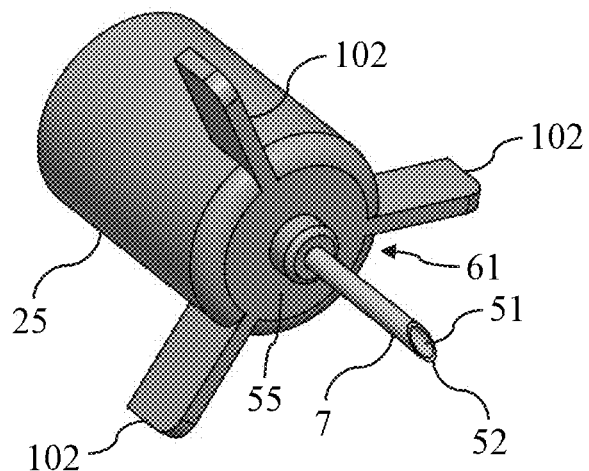
FIGS. 29 and 30 illustrate perspective views of a needle coupled to a barrel, according to some embodiments.
Figure 30:
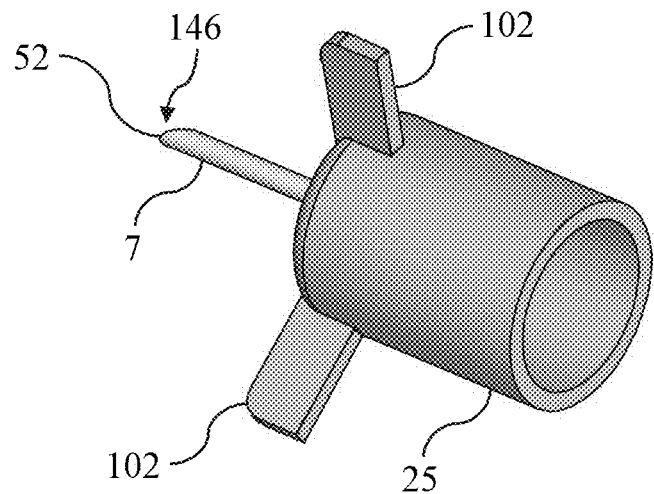
Figure 31:
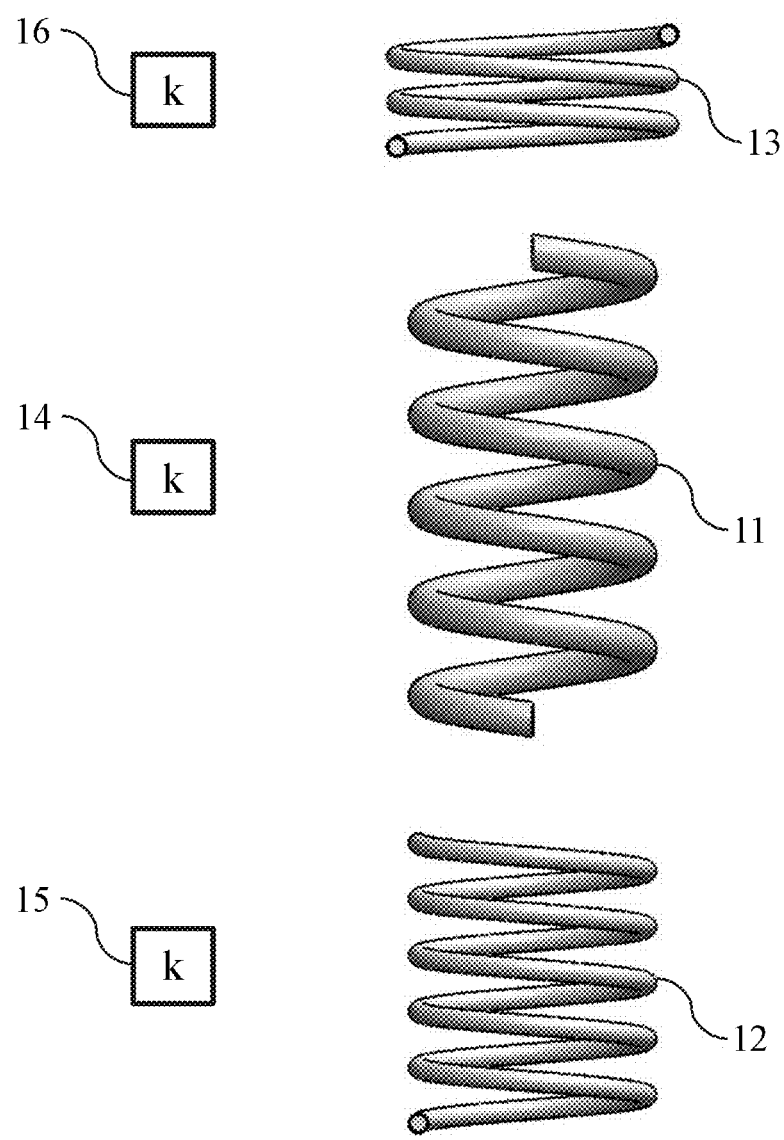
FIG. 31 illustrates a side view of three separate springs, according to some embodiments.
Figure 32:
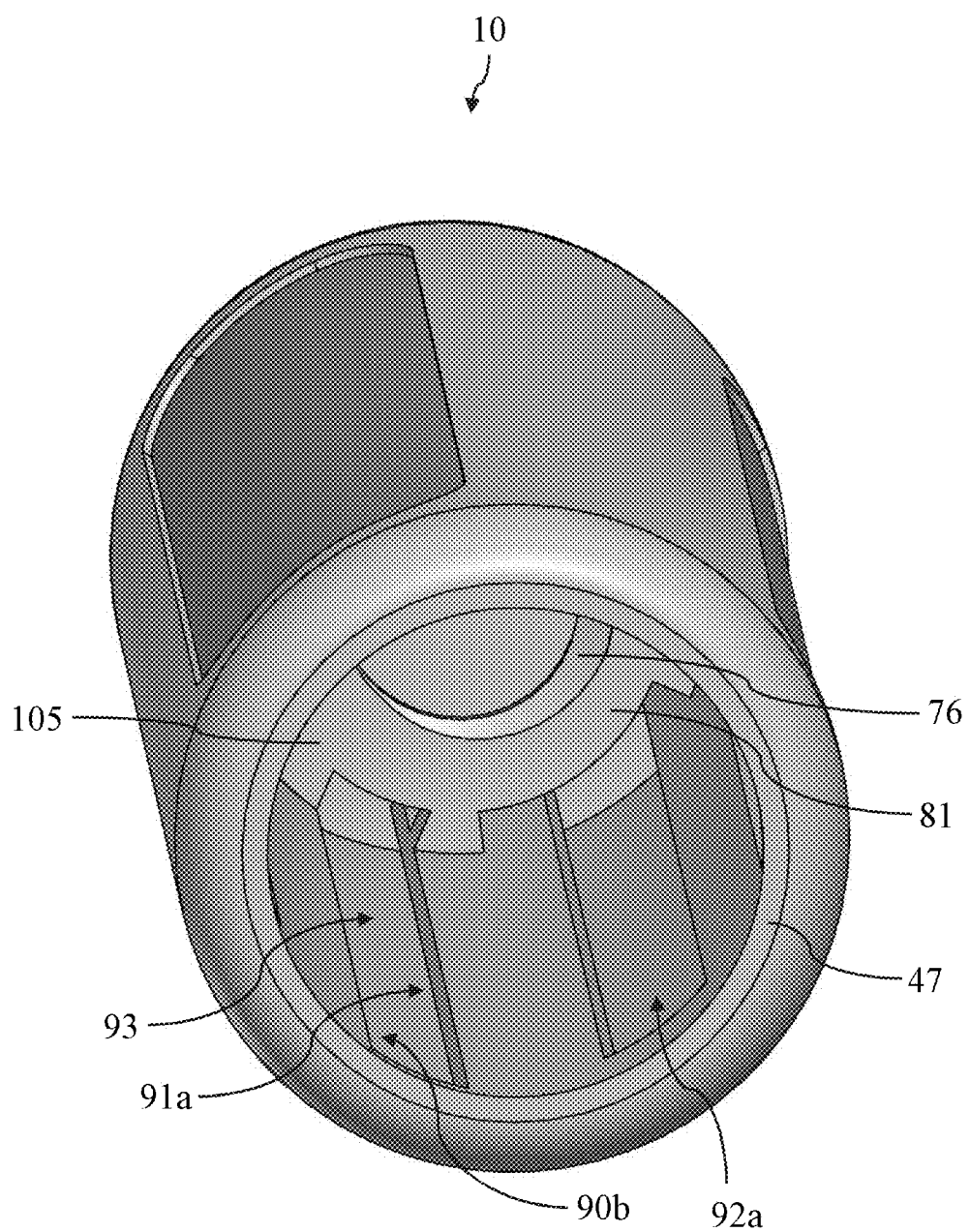
FIG. 32 illustrates a perspective view of an outer housing assembly, according to some embodiments.
Figure 33:
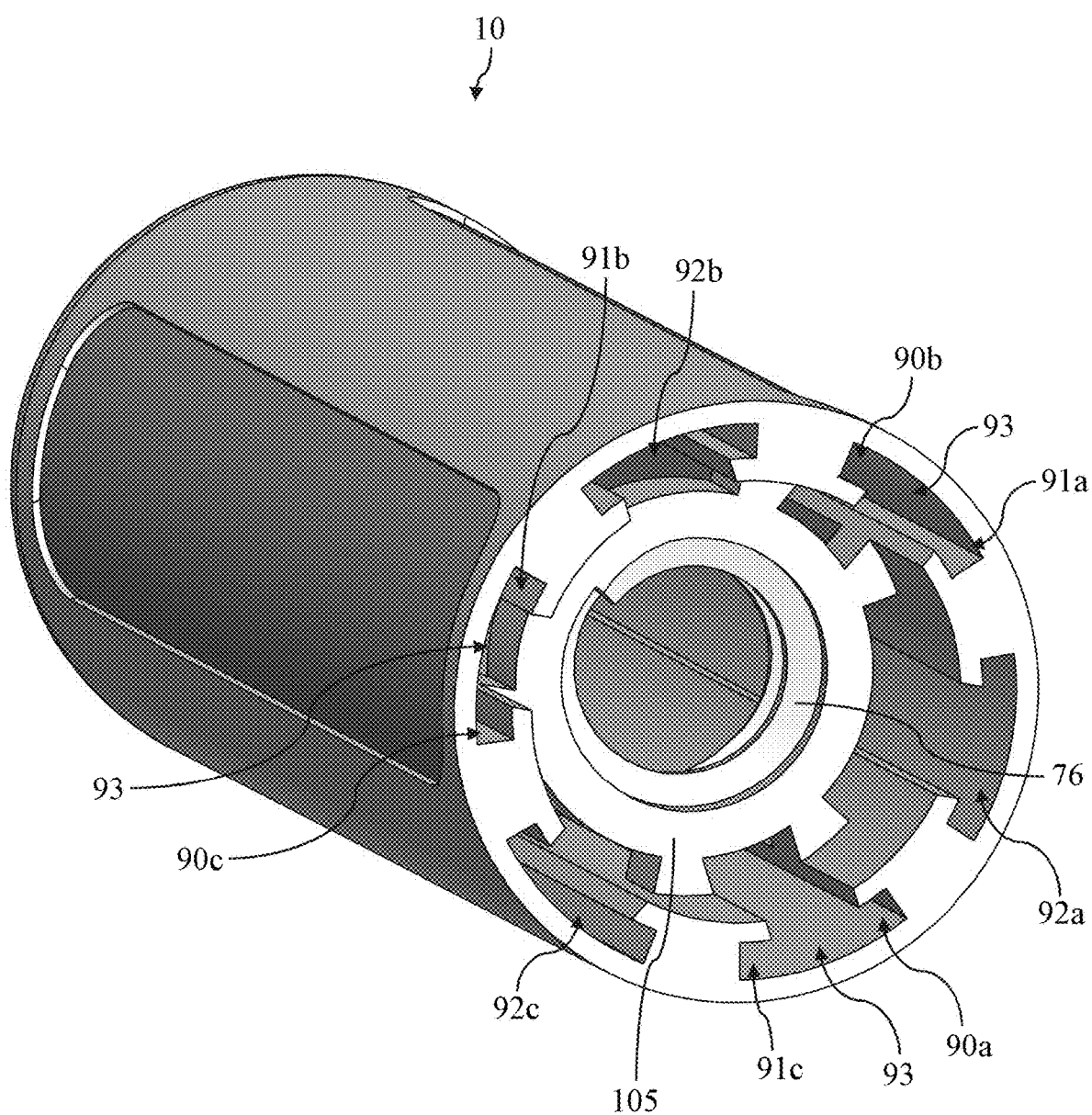
FIG. 33 illustrates a perspective view of an outer housing assembly with a proximal portion hidden, according to some embodiments.

FIG. 20 illustrates that the probes 40*a*, 40*b*, 40*c* have moved distally relative to rods 42*a*, 42*b*, 42*c* to enable the probes 40*a*, 40*b*, 40*c* to create the cylindrical sheath 141 around the deployed needle 7 as illustrated in FIG. 19. Note that the probes 40*a*, 40*b*, 40*c* are not rigidly coupled to the rods 42*a*, 42*b*, 42*c* and thus the probes 40*a*, 40*b*, 40*c* can push the rods 42*a*, 42*b*, 42*c* proximally, but the probes 40*a*, 40*b*, 40*c* can continue to move distally even after the rods 42*a*, 42*b*, 42*c* are prevented from continuing to move distally.

Many of the figures include a proximal direction arrow 27 and a distal direction arrow 28. The injector 2 can comprise a distal end 57 and a proximal end 58.

In order to increase the clarity of certain items and focus attention on particular items in each figure, not all items are labeled in each figure.

Rods described herein can have any of the features of any of the rods described herein. Each rod feature is not described in the context of every rod to avoid unnecessary redundancy. Probes described herein can have any of the features of any of the probes described herein. Each probe feature is not described in the context of every probe to avoid unnecessary redundancy.

Some embodiments have two rods and two probes. Some embodiments have three rods and three probes. Some embodiments have four rods and four probes. Some embodiments have many rods and many probes. Some embodiments have a first number of rods and a different number of probes.

Some embodiments are directed to an injector 2, which can be an auto-injector 2 used to inject medicine 3 into a person 29.

In some embodiments, an injector 2 comprises an outer housing assembly 10; a syringe 39 that has a barrel 25, a needle 7, and a plunger 22; and a first probe 40*a* that protrudes from a distal end 47 of the outer housing assembly 10. The first probe 40*a* can be slidably coupled to the outer housing assembly 10. The barrel 25 of the syringe 39 can hold a medicine 3. The plunger 22 can be slidably coupled at least partially inside the barrel 25 such that the plunger 22 is configured to push the medicine 3 out of the barrel 25 and out of the needle 7 (into a person 29). The needle 7 can be coupled to a distal end portion 61 of the barrel 25.

In some embodiments, the syringe 39 can be coupled to the outer housing assembly 10 such that the syringe 39 is located at least partially inside the outer housing assembly 10. The syringe 39 can be slidably coupled to the outer housing assembly 10 to enable the syringe 39 to move distally relative to the outer housing assembly 10 to inject a medicine 3 into a person 29.

In some embodiments, the injector 2 comprises a second probe 40*b* protruding from the distal end 47 of the outer housing assembly 10 and configured to move independently of the first probe 40*a*; a first rod 42*a* configured such that moving the first probe 40*a* proximally relative to the outer housing assembly 10 pushes the first rod 42*a* proximally to unlock the first rod 42*a* from the plunger 22; and a second rod 42*b* configured to move independently of the first rod 42a such that moving the second probe 40b proximally relative to the outer housing assembly 10 pushes the second rod 42b proximally to unlock the second rod 42b from the plunger 22.

The injector 2 can be configured such that unlocking both the first rod 42a and the second rod 42b from the plunger 22 enables the plunger 22 to rotate relative to the outer housing assembly 10 such that a first spring 11 pushes the needle 7 distally relative to the outer housing assembly 10 to inject a medicine 3 into a person 29.

FIG. 3C illustrates a first probe 40a contacting the person 29. Pressing the first probe 40a against the person 29 can push the first probe 40a proximally relative to the outer housing assembly 10 to unlock the first rod 42a. However, a second probe 40b does not contact the person 29 in FIG. 3C, so the second probe 40b does not move proximally relative to the outer housing assembly 10. As a result, the second rod 42b is not unlocked, which prevents deployment of the medicine 3 in a situation where the medicine 3 would be ejected outside 36 the person 29 due to the position of the injector 2 relative to the person 29. In some embodiments such as the embodiment illustrated in FIG. 3C, all three probes 40a, 40b, 40c must be pressed against the person 29 to enable the ejector 2 to deploy the medicine 3.

FIG. 13 illustrates a situation where a first probe 40a was moved proximally relative to an outer housing assembly 10 (which is hidden in FIG. 13) and a second probe 40b was not moved proximally relative to an outer housing assembly 10. This situation resulted in a first rod 42a moving proximally (such that the first rod 42a is unlocked) while a second rod 42b did not move proximally. As a result, the second rod 42b is still locked and the plunger 22 cannot move distally relative to the outer housing assembly 10.

In some embodiments, the outer housing assembly 10 comprises a radially inward protrusion 105 configured to limit a first distal movement 106 of the first rod 42a. The injector 2 can be configured to enable the first probe 40a to continue moving distally after the radially inward protrusion 105 limits the first distal movement 106 of the first rod 42a such that the first probe 40a is configured to block access to the needle 7 after the needle 7 injects a medicine 3.

Probes 40a, 40b, 40c can comprise a skin-contacting member 157 disposed at a distal end of the injector 2. Pressing the injector 2 against the person 29 can move the skin-contacting member proximally relative to the outer housing assembly 10.

In some embodiments, the plunger 22 comprises a first threaded portion 75 and the outer housing assembly 10 comprises a second threaded portion 76 that is threadably coupled with the first threaded portion 75. The injector 2 can be configured such that unlocking both the first rod 42a and the second rod 42b from the plunger 22 causes a spring force 107 of the first spring 11 to rotate the plunger 22 relative to the outer housing assembly 10 due to the first threaded portion 75 contacting the second threaded portion 76.

Some embodiments use low-friction materials, lubricants, and/or a large thread pitch to facilitate threaded rotation.

In some embodiments, an injector 2 comprises a second spring 12 located around at least a first portion 62 of the plunger 22. The second spring 12 can be compressed between a first radially outward protrusion 82 of the plunger 22 and at least one of the first probe 40a and the second probe 40b.

In some embodiments, a third spring 13 is compressed between a proximal end 94 of the outer housing assembly 10 and at least a second portion 71 of the first rod 42a such that the third spring 13 is configured to push the first rod 42a distally relative to the outer housing assembly 10. The injector 2 can be configured such that moving the first probe 40a proximally relative to the outer housing assembly 10 to push the first rod 42a proximally to unlock the first rod 42a from the plunger 22 requires overcoming a spring force 109 of the third spring 13.

In some embodiments, a proximal end 95 of the plunger 22 comprises at least one proximal protrusion 110, a proximal end 96 of the first rod 42a comprises a first radially inward protrusion 112, and the second rod 42b comprises a second radially inward protrusion 112 on a proximal end 96 of the second rod 42b.

In some embodiments, the first radially inward protrusion 112 and the second radially inward protrusion 112 are interlocked with the at least one proximal protrusion 110 of the plunger 22 such that the injector 2 is configured so the plunger 22 cannot rotate relative to the outer housing assembly 10 until after the first radially inward protrusion 112 and the second radially inward protrusion 112 move proximally relative to the at least one proximal protrusion 110.

In some embodiments, an angle 114 between the first radially inward protrusion 112 and the second radially inward protrusion 112 is 120 degrees and/or greater than 100 degrees and less than 140 degrees. A first proximal end portion 72a of the first rod 42a can comprise the first radially inward protrusion 112. A second proximal end portion 72b of the second rod 42b can comprise the second radially inward protrusion 112. A third proximal end portion 72c of the third rod 42c can comprise a third radially inward protrusion 112.

In some embodiments, a proximal end 95 of the plunger 22 comprises a first proximal protrusion 110, a second proximal protrusion 110, and a third proximal protrusion 110. The first proximal protrusion 110, the second proximal protrusion 110, and the third proximal protrusion 110 can form a first channel 115, a second channel 115, and a third channel 115 on a proximal end of the plunger 22.

In some embodiments, the first rod 42a comprises a first radially inward protrusion 112 located at least partially in the first channel 115 such that the first radially inward protrusion 112 blocks the plunger 22 from rotating relative to the outer housing assembly 10.

In some embodiments, the second rod 42b comprises a second radially inward protrusion 112 located at least partially in the second channel 115 such that the second radially inward protrusion 112 blocks the plunger 22 from rotating relative to the outer housing assembly 10.

In some embodiments, the third rod 42c comprises a third radially inward protrusion 112 located at least partially in the third channel 115 such that the third radially inward protrusion 112 blocks the plunger 22 from rotating relative to the outer housing assembly 10.

In some embodiments, the injector 2 is configured such that the plunger 22 cannot rotate relative to the outer housing assembly 10 to enable the needle 7 to move distally to inject a medicine 3 until after the first probe 40a moves proximally and thereby pushes the first rod 42a proximally to move the first radially inward protrusion 112 proximally out of the first channel 115; the second probe 40b moves proximally and thereby pushes the second rod 42b proximally to move the second radially inward protrusion 112 proximally out of the second channel 115; and the third probe 40c moves proximally and thereby pushes the third rod 42c proximally to move the third radially inward protrusion 112 proximally out of the third channel 115.

In some embodiments, the first probe 40*a* comprises a proximally facing end 116 that abuts a distally facing end 117 of the first rod 42*a*. The injector 2 can be configured such that the proximally facing end 116 pushes the distally facing end 117 proximally to move the first radially inward protrusion 112 proximally out of the first channel 115.

In some embodiments, the first probe 40*a* comprises a flex arm 118 configured to flex to enable distal movement 121 of the first probe 40*a* and then collide with a distal face 122 of the outer housing assembly 10 to prevent proximal movement 123 of the first probe 40*a*. The flex arm 118 can comprise a cantilever beam 73.

In some embodiments, the outer housing assembly 10 comprise a first groove 90*a* and a second groove 92*a* that are oriented from a distal end 47 of the outer housing assembly 10 to a proximal end 94 of the outer housing assembly 10.

As used herein, grooves and other items can be oriented from a distal end 47 of the outer housing assembly 10 to a proximal end 94 of the outer housing assembly 10 without actually reaching all the way from the distal end 47 to the proximal end 94.

The first probe 40*a* can comprise a first fin 100 slidably coupled to the first groove 90*a*. The first rod 42*a* can comprise a second fin 101 slidably coupled to the second groove 92*a*.

In some embodiments, the outer housing assembly 10 comprises a first groove 93. The barrel 25 can comprise a first radially outward protrusion 102 located at least partially between the first probe 40*a* and the second probe 40*b* such that the first probe 40*a* and the second probe 40*b* limit rotation 125 of the first radially outward protrusion 102 relative to a first central axis 79 of the outer housing assembly 10.

Figure 9:
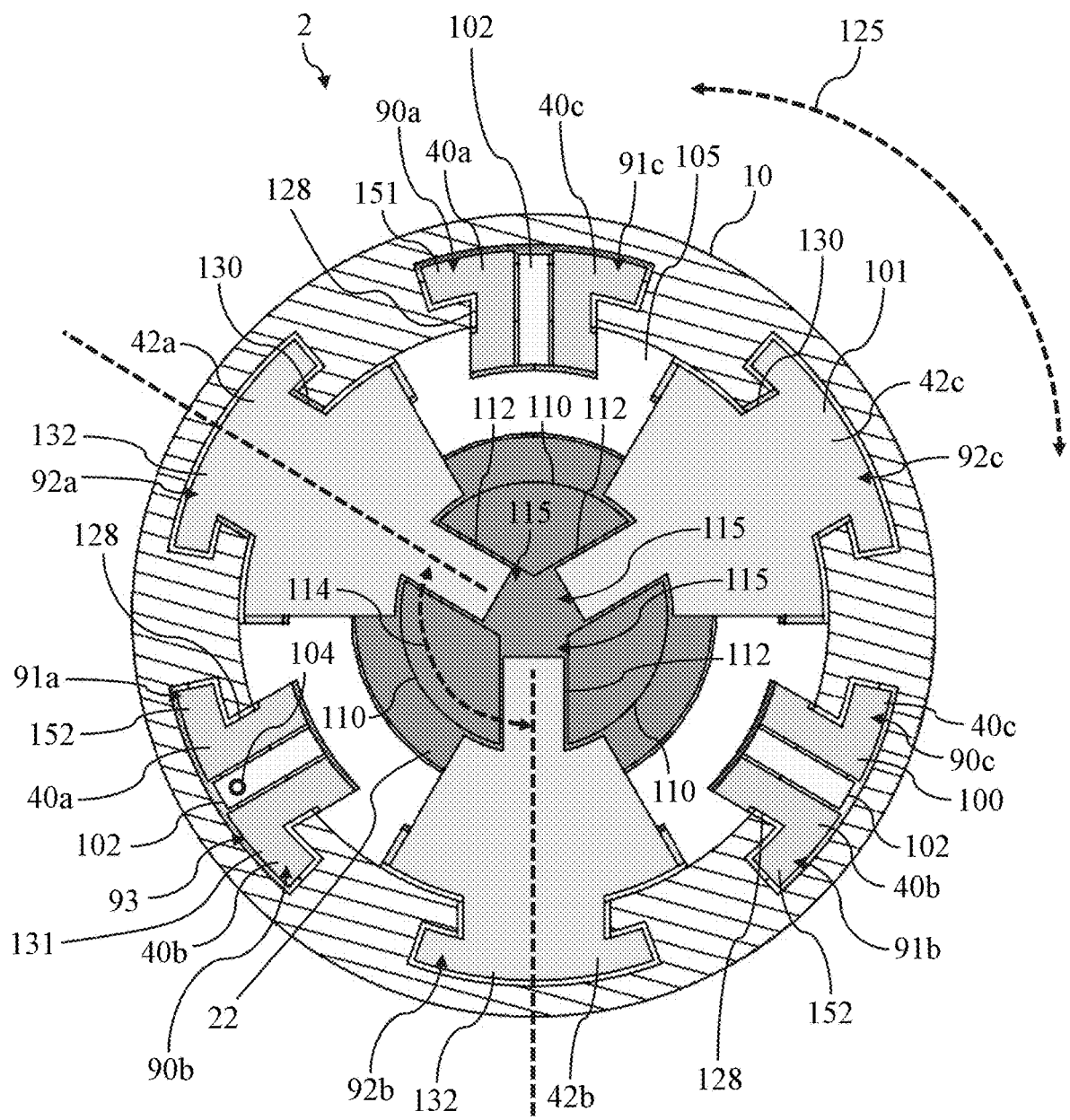
FIG. 9 illustrates a cross-sectional view of the injector taken along line 9 in FIG. 7, according to some embodiments.
Figure 10:
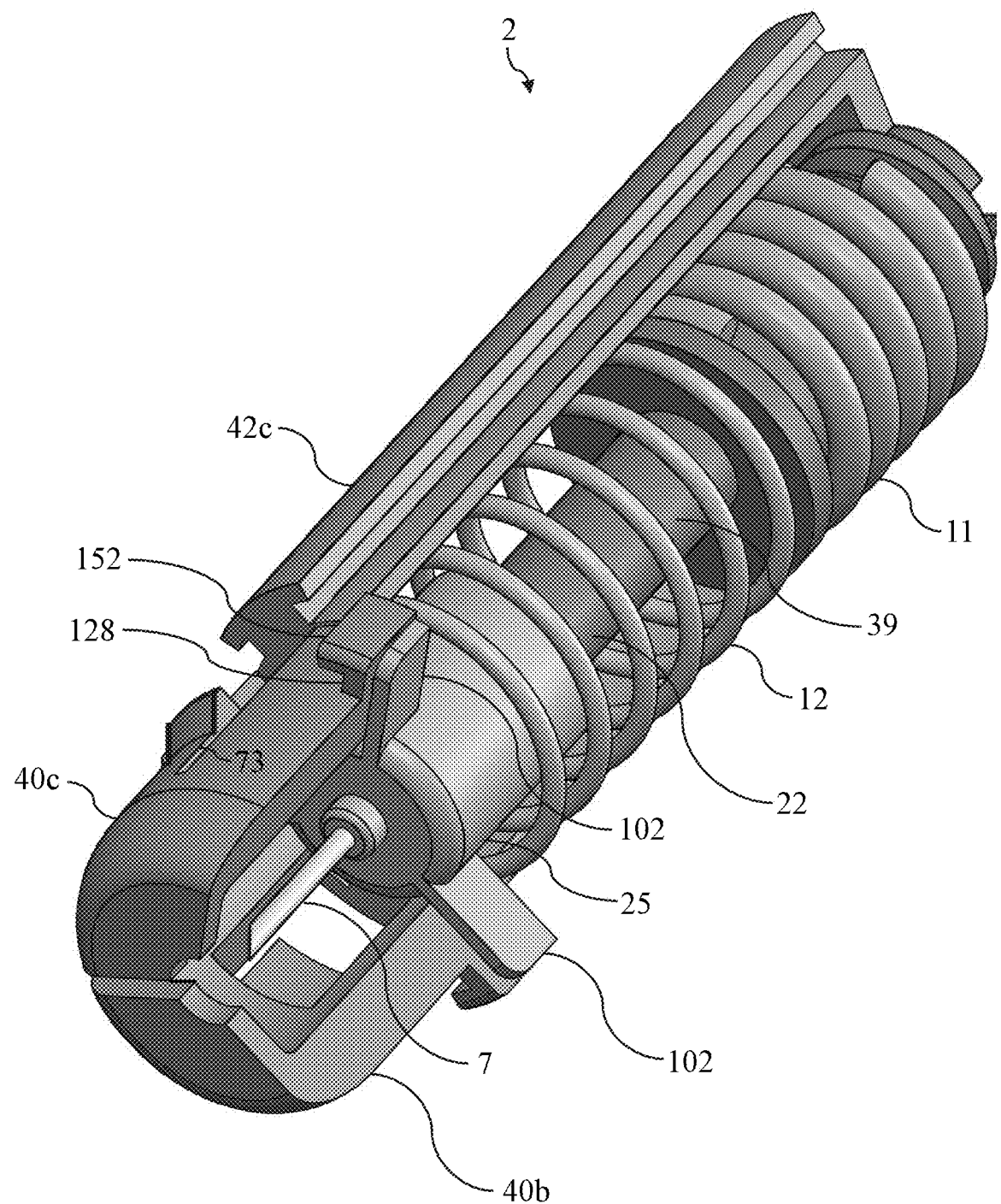
FIG. 10 illustrates a perspective view of the injector with an outer housing assembly, a rod, a spring, and a probe hidden, according to some embodiments.
Figure 11:
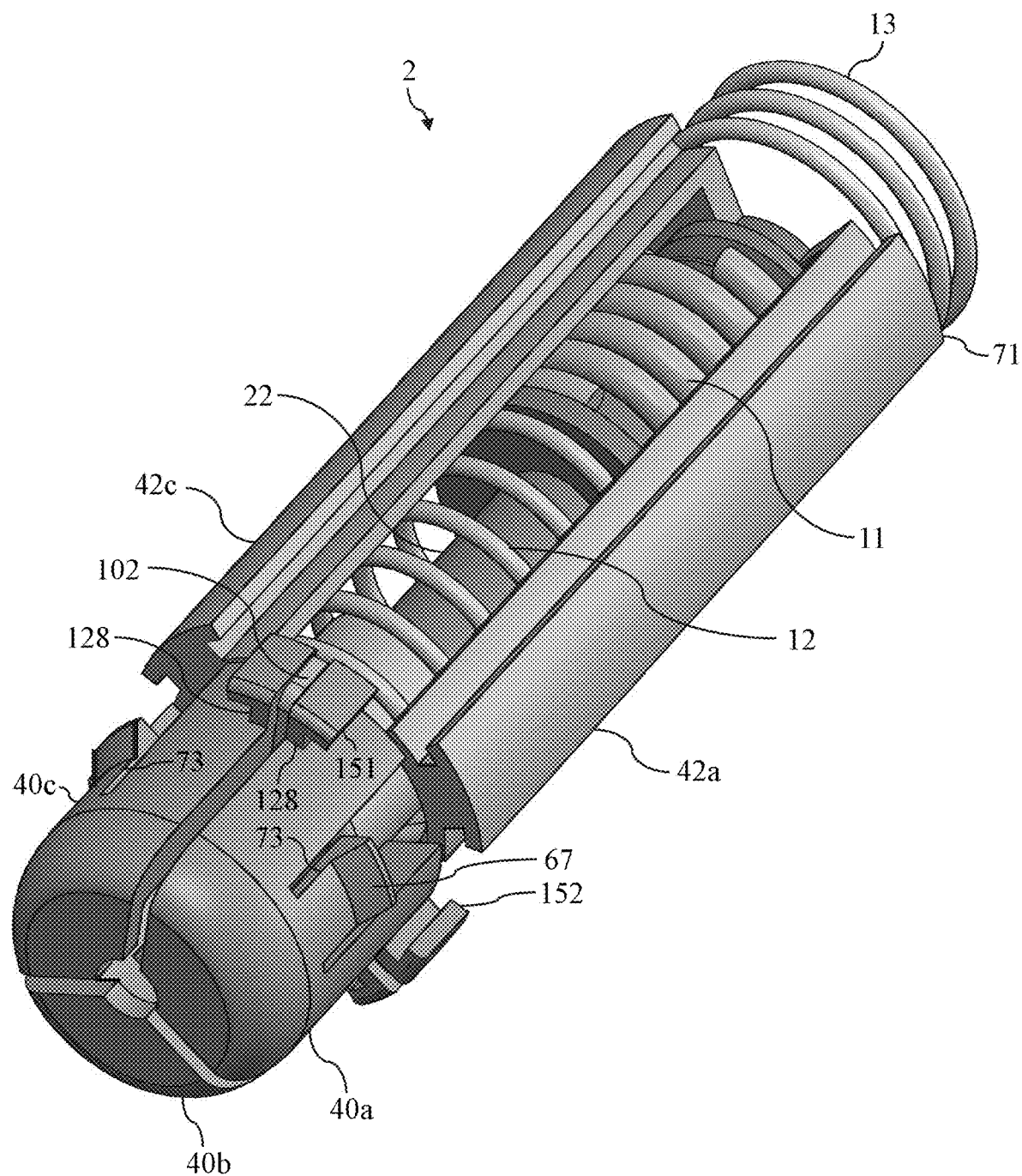
FIG. 11 illustrates a perspective view of the injector with an outer housing assembly hidden, according to some embodiments.

In some embodiments, the first probe 40*a*, the second probe 40*b*, and the first radially outward protrusions 102 are slidably coupled to the first groove 93 having a second central axis 104 that is oriented within ten degrees of parallel to the first central axis 79. (The second central axis 104 goes into the page as illustrated in FIG. 9.)

Groove 93 can be a T-shaped groove having a first groove 91*a* on one side and a second groove 90*b* on another side. Groove 93 can be a T-shaped groove having a first groove 91*b* on one side and a second groove 90*c* on another side. Groove 93 can be a T-shaped groove having a first groove 91*c* on one side and a second groove 90*a* on another side. Grooves 92*a*, 92*b*, and 92*c* can also be T-shaped grooves.

In some embodiments, the first probe 40*a* comprises a distally facing skin-contacting surface 127, a flex arm 118, a first radially outward protrusion 128, and a second radially outward protrusion 128, and the outer housing assembly 10 comprises a first groove 90*a* and a second groove 91*a*.

In some embodiments, the flex arm 118 is configured to flex to enable distal movement of the first probe 40*a* and then collide with a distal face 122 of the outer housing assembly 10 to prevent proximal movement 123 of the first probe 40*a*. The first radially outward protrusion 128 can be slidably coupled to the first groove 90*a* of the outer housing assembly 10. The second radially outward protrusion 128 can be slidably coupled to the second groove 91*a* of the outer housing assembly 10.

An outer housing assembly 10 can comprise many grooves 90*a*, 92*a*, 91*a*, 90*b*, 92*b*, 91*b*, 90*c*, 92*c*, 91*c*, 93. The grooves 90*a*, 92*a*, 91*a*, 90*b*, 92*b*, 91*b*, 90*c*, 92*c*, 91*c*, 93 can be oriented from a distal end of the outer housing assembly 10 to a proximal end of the outer housing assembly 10 such that the grooves 90*a*, 92*a*, 91*a*, 90*b*, 92*b*, 91*b*, 90*c*, 92*c*, 91*c*, 93 run at least partially along a length of the outer housing assembly 10 (but do not necessarily run all the way from the distal end of the outer housing assembly 10 to the proximal end of the outer housing assembly 10).

A first probe 40*a* can be slidably coupled to grooves 90*a*, 91*a* by protrusions 128 such that the first probe 40*a* can slide distally and proximally relative to the outer housing assembly 10. A first rod 42*a* can be slidably coupled to a groove 92*a* such that the first rod 42*a* can slide distally and proximally relative to the outer housing assembly 10. Moving the first probe 40*a* proximally relative to the outer housing assembly 10 can push the first rod 42*a* proximally relative to the outer housing assembly 10.

FIGS. 5 and 13 illustrate how the first probe 40*a* can abut the first rod 42*a* such that pushing the first probe 40*a* proximally relative to the outer housing 10 (e.g., by holding onto the outer housing assembly 10 while pressing a distal end 26 of the injector 2 against a person 29) can cause the first probe 40*a* to push the first rod 42*a* proximally relative to the outer housing assembly 10. A second probe 40*b* can push a second rod 42*b* in the same way. A third probe 40*c* can push a third rod 42*c* in the same way. A tenth probe can push a tenth rod in the same way. FIG. 13 also illustrates how the second probe 40*b* can abut the second rod 42*b*.

A second probe 40*b* can be slidably coupled to grooves 90*b*, 91*b* by protrusions 128 such that the second probe 40*b* can slide distally and proximally relative to the outer housing assembly 10. A second rod 42*b* can be slidably coupled to a groove 92*b* such that the second rod 42*b* can slide distally and proximally relative to the outer housing assembly 10. Moving the second probe 40*b* proximally relative to the outer housing assembly 10 (e.g., by holding onto the outer housing assembly 10 while pressing a distal end 26 of the injector 2 against a person 29) can push the second rod 42*b* proximally relative to the outer housing assembly 10.

A third probe 40*c* can be slidably coupled to grooves 90*c*, 91*c* by protrusions 128 such that the third probe 40*c* can slide distally and proximally relative to the outer housing assembly 10. A third rod 42*c* can be slidably coupled to a groove 92*c* such that the third rod 42*c* can slide distally and proximally relative to the outer housing assembly 10. Moving the third probe 40*c* proximally relative to the outer housing assembly 10 (e.g., by holding onto the outer housing assembly 10 while pressing a distal end 26 of the injector 2 against a person 29) can cause the third probe 40*c* to push the third rod 42*c* proximally relative to the outer housing assembly 10.

Figure 4:
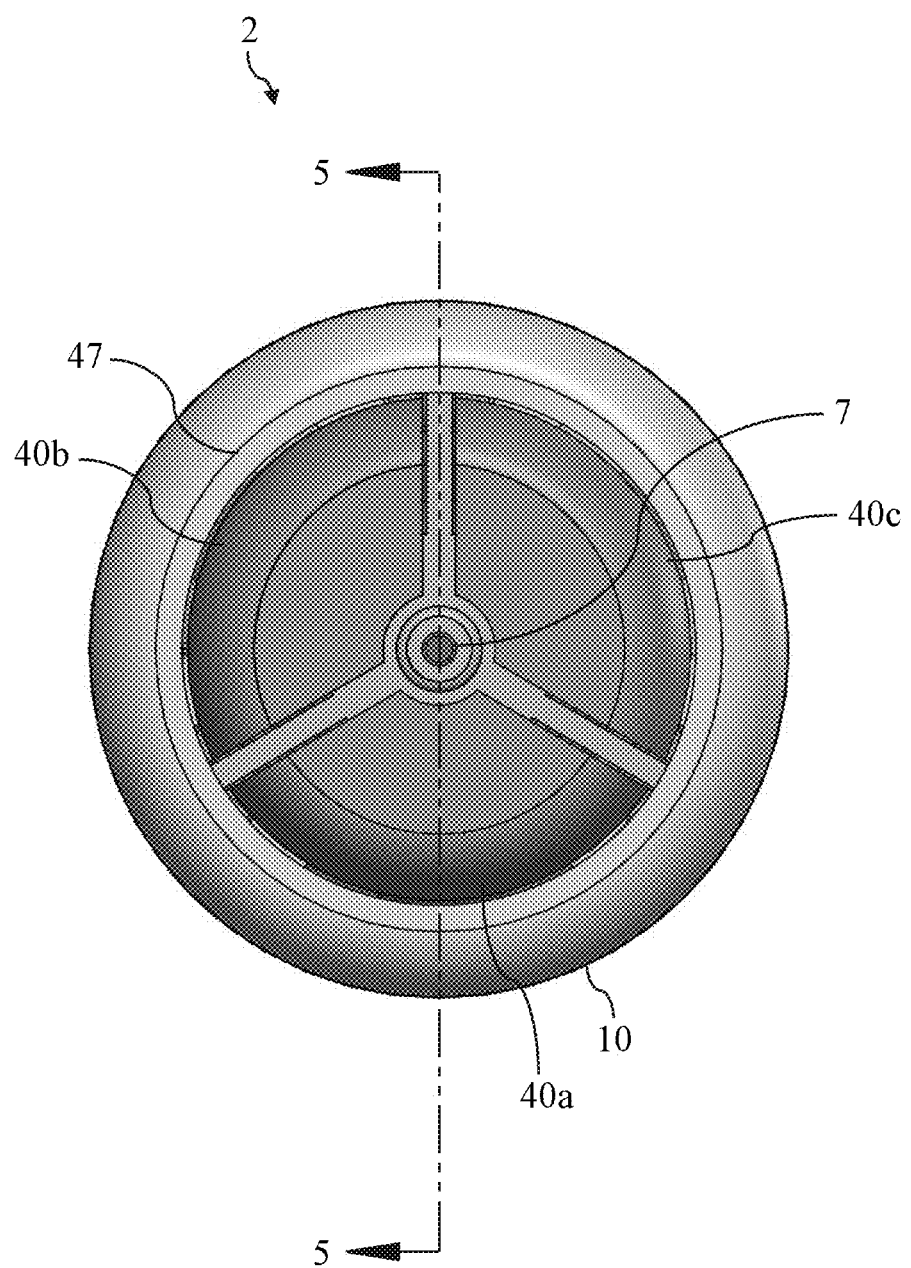
FIG. 4 illustrates a bottom view of the injector, according to some embodiments.

FIG. 4 illustrates a distal end of the injector 2. The injector 2 can comprise many probes 40*a*, 40*b*, 40*c*.

Figure 8:
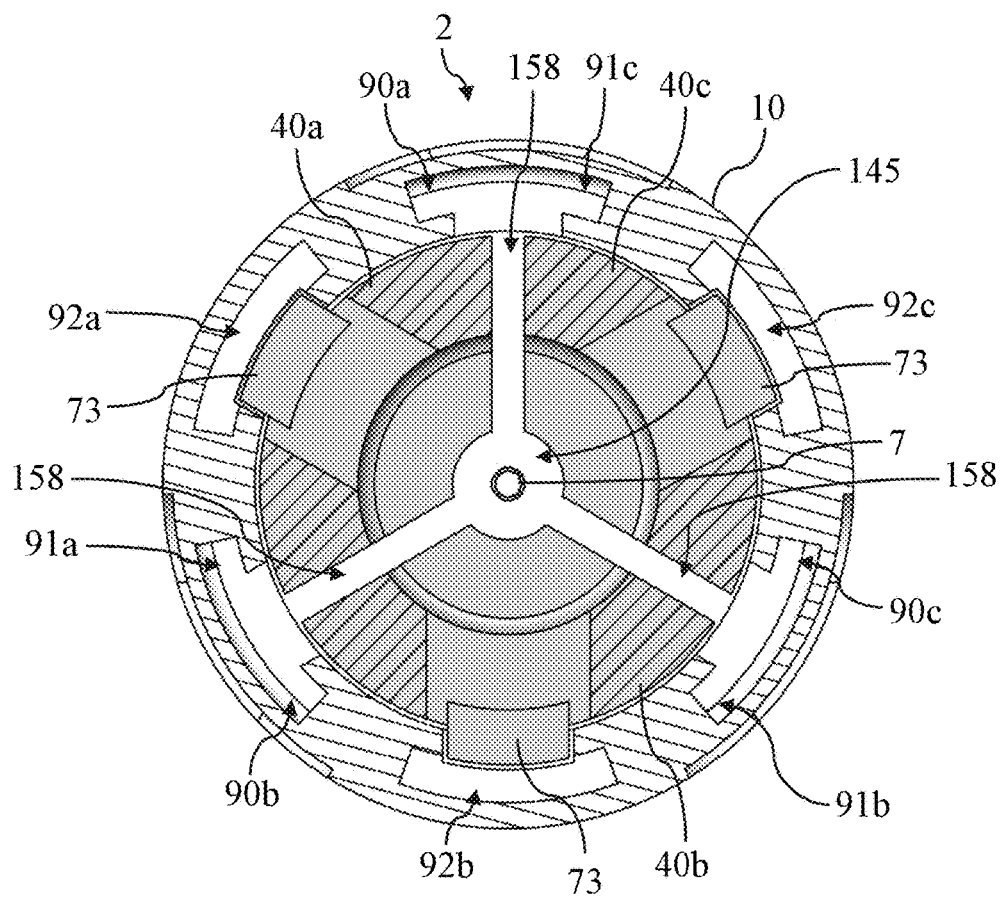
FIG. 8 illustrates a cross-sectional view of the injector taken along line 8 in FIG. 7, according to some embodiments.

Probes 40*a*, 40*b*, 40*c* can be separated from each other by gaps 158 (labeled in FIG. 8). Probes 40*a*, 40*b*, 40*c* can slide independently of each other relative to the outer housing assembly 10 such that some probes can move proximally relative to the outer housing assembly 10 while other probes do not move proximally relative to the outer housing assembly 10.

In some embodiments, the outer housing assembly 10 comprises a first groove 90*a*, a second groove 90*b*, a third groove 92*a*, and a fourth groove 92*b*. In some embodiments, grooves can be long, narrow channels.

In some embodiments, the first probe 40*a* is slidably coupled to the first groove 90*a*, the second probe 40*b* is slidable coupled to the second groove 90*b*, the first rod 42*a* is slidably coupled to the third groove 92*a*, and the second rod 42*b* is slidably coupled to the fourth groove 92*b* such that the first probe 40*a*, the second probe 40*b*, the first rod 42*a*, and the second rod 42*b* are configured to move proximally relative to the outer housing assembly 10 to enable the plunger 22 to rotate relative to the outer housing assembly 10.

In some embodiments, the first probe 40a comprises a first radially outward protrusion 128 that slidably couples the first probe 40a to the first groove 90a. The second probe 40b can comprise a second radially outward protrusion 128 that slidably couples the second probe 40b to the second groove 90b. The first rod 42a can comprise a third radially outward protrusion 130 that slidably couples the first rod 42a to the third groove 92a. The second rod 42b can comprise a fourth radially outward protrusion 130 that slidably couples the second rod 42b to the fourth groove 92b.

In some embodiments, the first probe 40a comprises a first L-shaped protrusion 131 that slidably couples the first probe 40a to the first groove 90a. The second probe 40b can comprise a second L-shaped protrusion 131 that slidably couples the second probe 40b to the second groove 90b. The first rod 42a can comprise a first T-shaped protrusion 132 that slidably couples the first rod 42a to the third groove 92a. The second rod 42b can comprise a second T-shaped protrusion 132 that slidably couples the second rod 42b to the fourth groove 92b.

In some embodiments, grooves 90a, 92a, 91a, 90b, 92b, 91b, 90c, 92c, 91c, 93 run from a distal portion 77 of the outer housing assembly 10 to a proximal portion 78 of the outer housing assembly 10.

In some embodiments, the outer housing assembly 10 comprises a central axis 79 from a distal portion 77 of the outer housing assembly 10 to a proximal portion 78 of the outer housing assembly 10; grooves 90a, 92a, 91a, 90b, 92b, 91b, 90c, 92c, 91c, 93 are oriented in a direction 133 from the distal portion 77 to the proximal portion 78, and the direction is within ten degrees of parallel to the central axis 79.

In some embodiments, the outer housing assembly 10 comprises a central axis 79 from a distal portion 77 of the outer housing assembly 10 to a proximal portion 78 of the outer housing assembly 10, the first groove 90a is oriented in a first direction 135 from the distal portion 77 to the proximal portion 78, the second groove 90b is oriented in a second direction 133 from the distal portion 77 to the proximal portion 78, the third groove 92a is oriented in a third direction 136 from the distal portion 77 to the proximal portion 78, the fourth groove 92b is oriented in a fourth direction 134 from the distal portion 77 to the proximal portion 78, and the first direction, the second direction, the third direction, and the fourth direction are within ten degrees of parallel to the central axis 79.

In some embodiments, an injector 2 comprises an outer housing assembly 10; a syringe 39 coupled at least partially inside the outer housing assembly 10 and having a barrel 25, a needle 7, and a plunger 22; and a first probe 40a protruding from a distal end 47 of the outer housing assembly 10.

In some embodiments, an injector 2 comprises a second probe 40b protruding from the distal end 47 of the outer housing assembly 10 and configured to move independently of the first probe 40a; and a third probe 40c protruding from the distal end 47 of the outer housing assembly 10 and configured to move independently of the first probe 40a and the second probe 40b.

In some embodiments, an injector 2 comprises a first rod 42a configured such that moving the first probe 40a proximally relative to the outer housing assembly 10 pushes the first rod 42a proximally to unlock the first rod 42a from the plunger 22; a second rod 42b configured to move independently of the first rod 42a such that moving the second probe 40b proximally relative to the outer housing assembly 10 pushes the second rod 42b proximally to unlock the second rod 42b from the plunger 22; and a third rod 42c configured to move independently of the first rod 42a and the second rod 42b such that moving the third probe 40c proximally relative to the outer housing assembly 10 pushes the third rod 42c proximally to unlock the third rod 42c from the plunger 22.

In some embodiments, an injector 2 comprises a first spring 11 configured to push the plunger 22 distally relative to the outer housing assembly 10. The injector 2 can be configured such that unlocking the first rod 42a, the second rod 42b, and the third rod 42c from the plunger 22 enables the plunger 22 to move distally relative to the outer housing assembly 10 such that the first spring 11 pushes the plunger 22 distally relative to the outer housing assembly 10 to inject a medicine 3 into a person 29.

Some embodiments consist of two rods such that just unlocking the first rod 42a but not unlocking the second rod 42b will not enable the plunger 22 to move distally relative to the outer housing because the second rod 42b prevents the distal movement. Thus, in some embodiments, both rods 42a, 42b must be unlocked before the plunger 22 can move distally relative to the outer housing to inject the medicine 3.

Some embodiments consist of three rods such that just unlocking the first rod 42a and the second rod 42b but not unlocking the third rod 42c will not enable the plunger 22 to move distally relative to the outer housing because the third rod 42c prevents the distal movement. Thus, in some embodiments all three rods 42a, 42b, 42c must be unlocked before the plunger 22 can move distally relative to the outer housing to inject the medicine 3.

Some embodiments consist of more than three rods such that unlocking all the rods is necessary to enable the plunger 22 to move distally relative to the outer housing.

After an injector 2 is used to inject medicine 3 into a person, an exposed needle 7 can inadvertently puncture another person 37, which can transmit diseases. Many embodiments include features to protect people from needle-stick punctures 142.

In some embodiments, the injector 2 is configured such that after the medicine 3 is injected, the first probe 40a, the second probe 40b, and the third probe 40c move distally relative to the outer housing assembly 10 to form a sheath 141 that blocks a distal end 52 of the needle 7 from punctures 142.

In some embodiments, the first probe 40a, the second probe 40b, and the third probe 40c are spaced radially outward around a perimeter 143 of the needle 7.

In some embodiments, an injector 2 comprises a second spring 12 located around at least a first portion 62 of the plunger 22 and compressed between a first radially outward protrusion 82 of the plunger 22 and at least one of the first probe 40a and the second probe 40b.

In some embodiments, an injector 2 comprising a third spring 13 compressed between a proximal end 94 of the outer housing assembly 10 and at least a second portion 71 of the first rod 42a such that the third spring 13 is configured to push the first rod 42a, the second rod 42b, and the third rod 42c distally relative to the outer housing assembly 10. The injector 2 can be configured such that moving the first probe 40a, the second probe 40b, and the third probe 40c proximally relative to the outer housing assembly 10 to push the first rod 42a, the second rod 42b, and the third rod 42c proximally to unlock the first rod 42a, the second rod 42b, and the third rod 42*c* from the plunger 22 requires overcoming a spring force 109 of the third spring 13 by compressing the third spring 13.

In some embodiments, a first rod 42*a* is slidably coupled to the outer housing assembly 10 and configured such that moving the first probe 40*a* proximally (relative to the outer housing assembly 10) pushes the first rod 42*a* proximally (relative to the outer housing assembly 10) to unlock the first rod 42*a* from the plunger 22.

In some embodiments, a second rod 42*b* is slidably coupled to the outer housing assembly 10 and configured to move independently of the first rod 42*a* such that moving the second probe 40*b* proximally (relative to the outer housing assembly 10) pushes the second rod 42*b* proximally (relative to the outer housing assembly 10) to unlock the second rod 42*b* from the plunger 22.

Some embodiments comprise an injector 2, which can comprise an outer housing assembly 10; a syringe 39 coupled at least partially inside the outer housing assembly 10 and having a barrel 25, a needle 7, and a plunger 22; and a first probe 40*a* slidably coupled to the outer housing assembly 10 and protruding from a distal end 47 of the outer housing assembly 10. The plunger 22 can be slidably coupled to the barrel 25 such that at least a portion 65 of the plunger 22 is located inside the barrel 25 and such that the plunger 22 is configured to push medicine 3 located inside the barrel 25 out through a needle 7 into a person 29. The needle 7 can be coupled to a distal end 55 of the barrel 25. The needle 7 can comprise a lumen 51 located along a central axis of the needle 7 such that the lumen 51 carries medicine 3 from the barrel 25 into the person 29. A distal end 59 of the plunger 22 can comprise a seal 23 configured to prevent leaking of the medicine 3. This leak prevention forces the medicine 3 out of the needle 7 when the plunger 22 moves distally relative to the barrel 25.

In some embodiments, an injector 2 comprises a second probe 40*b* slidably coupled to the outer housing assembly 10, protruding from the distal end 47 of the outer housing assembly 10, and configured to move independently of the first probe 40*a*. The injector 2 can be configured such that moving both the first probe 40*a* and the second probe 40*b* proximally relative to the outer housing assembly 10 unlocks the plunger 22 such that the plunger 22 moves distally relative to the outer housing assembly 10 to inject a medicine 3 through the needle 7. The injector 2 can be configured such that moving the first probe 40*a* proximally (relative to the outer housing assembly 10) without moving the second probe 40*b* proximally (relative to the outer housing assembly 10) does not unlock the plunger 22 and such that moving the second probe 40*b* proximally (relative to the outer housing assembly 10) without moving the first probe 40*a* proximally (relative to the outer housing assembly 10) does not unlock the plunger 22.

In some embodiments, an injector 2 comprises a first spring 11 located around at least a first portion 63 of the plunger 22 and compressed between a second portion 81 of the outer housing assembly 10 and a radially outward protrusion 82 of the plunger 22. The injector 2 can be configured such that moving both the first probe 40*a* and the second probe 40*b* proximally relative to the outer housing assembly 10 unlocks the plunger 22 such that the first spring 11 moves the plunger 22 distally relative to the outer housing assembly 10 to inject the medicine 3 through the needle 7 into a person 29.

In some embodiments, an injector 2 comprises a third probe 40*c* slidably coupled to the outer housing assembly 10, protruding from the distal end 47 of the outer housing assembly 10, and configured to move independently of the first probe 40*a* and the second probe 40*b*. The first probe 40*a*, the second probe 40*b*, and the third probe 40*c* can form a cylindrical sheath 141 around the needle 7. The cylindrical sheath 141 can comprise a distal opening 145 configured to enable a distal tip 146 of the needle to exit the distal opening 145 to inject the medicine 3.

In some embodiments, an injector 2 is configured such that moving the plunger 22 distally relative to the outer housing assembly 10 to inject the medicine 3 requires moving the first probe 40*a*, the second probe 40*b*, and the third probe 40*c* proximally relative to the outer housing assembly 10.

The first probe 40*a* can be slidably coupled by radially outward protrusions 128 to grooves 90*a*, 91*a*. The first probe 40*a* can be configured to slide distally and proximally along grooves 90*a*, 91*a* relative to the outer housing assembly 10.

The second probe 40*b* can be slidably coupled by radially outward protrusions 128 to grooves 90*b*, 91*b*. The second probe 40*b* can be configured to slide distally and proximally along grooves 90*b*, 91*b* relative to the outer housing assembly 10.

In some embodiments, the outer housing assembly 10 comprises a first groove 90*a* and a second groove 90*b* that are oriented from a distal portion 77 of the outer housing assembly 10 to a first proximal portion 78 of the outer housing assembly 10. The first probe 40*a* can comprise a first radially outward protrusion 128 that slidably couples the first probe 40*a* to the first groove 90*a*. The second probe 40*b* can comprise a second radially outward protrusion 128 that slidably couples the second probe 40*b* to the second groove 90*b*.

In some embodiments, the outer housing assembly 10 comprises a third groove 91*a* and a fourth groove 91*b* that are oriented from the distal portion 77 of the outer housing assembly 10 to the first proximal portion 78 of the outer housing assembly 10. The first probe 40*a* can comprise a third radially outward protrusion 128 that slidably couples the first probe 40*a* to the third groove 91*a*. The second probe 40*b* can comprise a fourth radially outward protrusion 128 that slidably couples the second probe 40*b* to the fourth groove 91*b*.

In some embodiments, the first probe 40*a* comprises a proximally protruding cantilever beam 73 having a second proximal portion 74 that comprises a ramp 67 that protrudes radially outward into a cavity 84 of the outer housing assembly 10. As illustrated in FIG. 5, the injector 2 can be configured such that the ramp 67 impedes a first distal movement 148 of the first probe 40*a* relative to the outer housing assembly 10 until a second distal movement 149 (illustrated in FIG. 17) of the plunger 22 relative to the outer housing assembly 10 causes a force 150 large enough to flex the cantilever beam 73 such that the ramp 67 moves radially inward out of the cavity 84.

Any of the probes described herein can comprise any of the features described in the context of the first probe 40*a*. The features are not described in the context of every probe to avoid unnecessary redundancy.

Any of the rods described herein can comprise any of the features described in the context of the first rod 42*a*. The features are not described in the context of every rod to avoid unnecessary redundancy.

In some embodiments, an injector 2 comprises a first spring 11 located around at least a first portion 63 of the plunger 22 and compressed between a second portion 81 of the outer housing assembly 10 and a fifth radially outward protrusion 82 of the plunger 22. The injector 2 can be configured such that moving both the first probe 40*a* and the second probe 40*b* proximally (relative to the outer housing assembly 10) unlocks the plunger 22 such that the first spring 11 moves the plunger 22 distally (relative to the outer housing assembly 10) to cause the force.

In some embodiments, a fifth protrusion 151 is coupled to the first probe 40*a* by the first radially outward protrusion 128; a sixth protrusion 152 is coupled to the first probe 40*a* by the third radially outward protrusion 128; a seventh protrusion 151 is coupled to the second probe 40*b* by the second radially outward protrusion 128; and an eighth protrusion 152 is coupled to the second probe 40*b* by the fourth radially outward protrusion 128. The fifth protrusion 151 and the sixth protrusion 162 can protrude toward each other to slidably couple the first probe 40*a* to grooves 90*a*, 91*a* of the outer housing assembly 10. The seventh protrusion 151 and the eight protrusion 152 can protrude toward each other to slidably couple the second probe 40*b* to grooves 90*b*, 91*b* of the outer housing assembly 10.

In some embodiments, an injector 2 comprises a first rod 42*a* slidably coupled to the outer housing assembly 10 and configured such that moving the first probe 40*a* proximally relative to the outer housing assembly 10 unlocks the first rod 42*a* from the plunger 22 by pushing the first rod 42*a* proximally relative to the outer housing assembly 10.

In some embodiments, an injector 2 comprises a second rod 42*b* slidably coupled to the outer housing assembly 10 and configured such that moving the second probe 40*b* proximally relative to the outer housing assembly 10 unlocks the second rod 42*b* from the plunger 22 by pushing the second rod 42*b* proximally relative to the outer housing assembly 10.

In some embodiments, an injector 2 comprises a first spring 11 configured to push the plunger 22 distally relative to the outer housing assembly 10. The injector 2 can be configured such that unlocking the first rod 42*a* and the second rod 42*b* from the plunger 22 enables the plunger 22 to move distally relative to the outer housing assembly 10 such that the first spring 11 pushes the plunger 22 distally relative to the outer housing assembly 10 to inject the medicine 3 into a person 29.

In some embodiments, the outer housing assembly 10 comprises a first groove 90*a*, a second groove 90*b*, a third groove 92*a*, and a fourth groove 92*b* that are oriented from a distal portion 77 of the outer housing assembly 10 to a proximal portion 78 of the outer housing assembly 10. The first probe 40*a*, the second probe 40*b*, the first rod 42*a*, and the second rod 42*b* can be slidably coupled to at least one of the first groove 90*a*, the second groove 90*b*, the third groove 92*a*, and the fourth groove 92*b* such that the first probe 40*a*, the second probe 40*b*, the first rod 42*a*, and the second rod 42*b* can move proximally relative to the outer housing assembly 10 by sliding along tracks of the first groove 90*a*, the second groove 90*b*, the third groove 92*a*, and the fourth groove 92*b*.

In some embodiments, the outer housing assembly 10 comprises a central axis 79 from the distal portion 77 of the outer housing assembly 10 to the proximal portion 78 of the outer housing assembly 10. The first groove, the second groove, the third groove, and the fourth groove can be oriented within ten degrees of parallel to the central axis 79 and/or within twenty degrees of parallel to the central axis 79.

In some embodiments, the first probe 40*a* comprises a first L-shaped protrusion 131 and a second L-shaped protrusion 131 that slidably couple the first probe 40*a* to at least one of the first groove 90*a*, the second groove 90*b*, the third groove 92*a*, and the fourth groove 92*b*.

In some embodiments, the first rod 42*a* comprises a first T-shaped protrusion 132 that slidably couples the first rod 42*a* to at least one of the first groove 90*a*, the second groove 90*b*, the third groove 92*a*, and the fourth groove 92*b*.

Any of the rods described herein can have any of the features described in the context of one or more rods described herein. To avoid unnecessary redundancy, not all features are described in the context of each individual rod. Any of the probes described herein can have any of the features described in the context of one or more probes described herein. To avoid unnecessary redundancy, not all features are described in the context of each individual probe.

In some embodiments, an injector 2 comprises a second spring 12 located around at least a first portion 62 of the plunger 22 and compressed between a first radially outward protrusion 82 of the plunger 22 and at least one of the first probe 40*a* and the second probe 40*b*. The second spring 12 can be configured to push the first probe 40*a* and the second probe 40*b* distally relative to the outer housing assembly 10 to cause the first probe 40*a* and the second probe 40*b* to move distally relative to the outer housing assembly 10 to hide the needle 7 after the needle 7 has injected the medicine 3. Hiding the needle 7 can prevent needlestick injuries.

In some embodiments, an injector 2 comprises a third spring 13 compressed between a proximal end 94 of the outer housing assembly 10 and a second portion 71 of the first rod 42*a* such that the third spring 13 is configured to push the first rod 42*a* and the second rod 42*b* distally relative to the outer housing assembly 10. The injector 2 can be configured such that moving the first probe 40*a* and the second probe 40*b* proximally relative to the outer housing assembly 10 to push the first rod 42*a* and the second rod 42*b* proximally (relative to the outer housing assembly 10) to unlock the first rod 42*a* and the second rod 42*b* from the plunger 22 requires overcoming a spring force 109 of the third spring 13.

In some embodiments, the first spring 11 has a first spring constant 14 that is at least twice a second spring constant 15 of the second spring 12. In some embodiments, the first spring 11 has a first spring constant 14 that is at least twice a third spring constant 16 of the third spring 13 and/or at least three times the third spring constant 16 of the third spring 13. In some embodiments, the second spring 12 has a second spring constant 15 that is at least twice a third spring constant 16 of the third spring 13. The relatively high first spring constant 14 of the first spring 11 relative to the second spring 12 and the third spring 13 enables the first spring 11 to dominate the second spring 12 and the third spring 13. This way, the first spring 11 can overpower the second spring 12 such that the strong force of the first spring 11 enables the first spring 11 to compress the second spring 12. The relatively low spring constant of the third spring 13 makes it relatively easy to move the first probe 40*a* and the second probe 40*b* proximally relative to the outer housing assembly 10 and thereby push the first rod 42*a* and the second rod 42*b* proximally to unlock the first rod 42*a* and the second rod 42*b* from the plunger 22 to enable the first spring 11 to drive the plunger 22 distally (relative to the outer housing assembly 10) to inject the medicine 3.

In some embodiments, an injector 2 comprises a third probe 40*c* slidably coupled to the outer housing assembly 10. The injector 2 can be configured such that after the medicine 3 is injected, the first probe 40*a*, the second probe 40*b*, and the third probe 40*c* move distally relative to the outer housing assembly 10 to form a cylindrical sheath 141 that blocks a distal end 52 of the needle 7 from needlestick punctures 142. The cylindrical sheath 141 can protect people administering injections from needlestick punctures 142.

In some embodiments, the first probe 40a, the second probe 40b, and the third probe 40c are spaced radially outward around a perimeter 143 of the needle 7.

In some embodiments, a first rod 42a comprises a first radially inward protrusion 112 and the second rod 42b comprises a second radially inward protrusion 112. The first radially inward protrusion 112 and the second radially inward protrusion 112 can lock the plunger 22 relative to the outer housing assembly 10 such that the plunger 22 cannot move distally relative to the outer housing assembly 10.

In some embodiments, the first rod 42a and the second rod 42b are at least 30 millimeters long as measured along a central axis 79 of the outer housing assembly 10.

In some embodiments, the first probe 40a comprises a proximally facing end 116 that abuts a distally facing end 117 of the first rod 42a, and the injector 2 is configured such that the proximally facing end 116 pushes the distally facing end 117 proximally.

In some embodiments, the outer housing assembly 10 is configured to limit a maximum distal movement 155 of the first rod 42a such that the first probe 40a is configured to continue moving distally after the outer housing assembly 10 prevents further distal movement 106 of the first rod 42a.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1, and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

The following is claimed:

1. An injector comprising:
   an outer housing assembly;
   a syringe coupled at least partially inside the outer housing assembly and having a barrel, a needle, and a plunger;
   a first probe protruding from a distal end of the outer housing assembly;
   a second probe protruding from the distal end of the outer housing assembly and configured to move independently of the first probe;
   a first rod slidably coupled to the outer housing assembly and configured such that moving the first probe proximally relative to the outer housing assembly pushes the first rod proximally to unlock the first rod from the plunger; and
   a second rod slidably coupled to the outer housing assembly and configured to move independently of the first rod such that moving the second probe proximally relative to the outer housing assembly pushes the second rod proximally to unlock the second rod from the plunger, wherein the injector is configured such that unlocking both the first rod and the second rod from the plunger enables the plunger to rotate relative to the outer housing assembly such that a first spring pushes the needle distally relative to the outer housing assembly.

2. The injector of claim 1, wherein the outer housing assembly comprises a radially inward protrusion configured to limit a first distal movement of the first rod, and the injector is configured to enable the first probe to continue moving distally after the radially inward protrusion limits the first distal movement of the first rod such that the first probe is configured to block access to the needle after the needle injects a medicine.

3. The injector of claim 1, wherein the plunger comprises a first threaded portion and the outer housing assembly comprises a second threaded portion that is threadably coupled with the first threaded portion, wherein the injector is configured such that unlocking both the first rod and the second rod from the plunger causes a spring force of the first spring to rotate the plunger relative to the outer housing assembly due to the first threaded portion contacting the second threaded portion.

4. The injector of claim 1, further comprising a second spring located around at least a first portion of the plunger and compressed between a first radially outward protrusion of the plunger and at least one of the first probe and the second probe, and
   the injector further comprising a third spring compressed between a proximal end of the outer housing assembly and at least a second portion of the first rod such that the third spring is configured to push the first rod distally relative to the outer housing assembly, wherein the injector is configured such that moving the first probe proximally relative to the outer housing assembly to push the first rod proximally to unlock the first rod from the plunger requires overcoming a spring force of the third spring.

5. The injector of claim 1, wherein a proximal end of the plunger comprises at least one proximal protrusion, the first rod comprises a first radially inward protrusion, the second rod comprises a second radially inward protrusion, the first radially inward protrusion and the second radially inward protrusion are interlocked with the at least one proximal protrusion of the plunger such that the injector is configured so the plunger cannot rotate relative to the outer housing assembly until after the first radially inward protrusion and the second radially inward protrusion move proximally relative to the at least one proximal protrusion.

6. The injector of claim 5, wherein an angle between the first radially inward protrusion and the second radially inward protrusion is greater than 100 degrees and less than 140 degrees, a first proximal end portion of the first rod comprises the first radially inward protrusion, and a second proximal end portion of the second rod comprises the second radially inward protrusion.

7. The injector of claim 1, wherein a proximal end of the plunger comprises at least a first proximal protrusion and a second proximal protrusion that form a first channel and a second channel,
   the first rod comprises a first radially inward protrusion located at least partially in the first channel such that the first radially inward protrusion blocks the plunger from rotating relative to the outer housing assembly,
   the second rod comprises a second radially inward protrusion located at least partially in the second channel such that the second radially inward protrusion blocks the plunger from rotating relative to the outer housing assembly, and
   the injector is configured such that the plunger cannot rotate relative to the outer housing assembly to enable the needle to move distally to inject a medicine until after the first probe moves proximally and thereby pushes the first rod proximally to move the first radially inward protrusion proximally out of the first channel and the second probe moves proximally and thereby pushes the second rod proximally to move the second radially inward protrusion proximally out of the second channel.

8. The injector of claim 7, wherein the first probe comprises a proximally facing end that abuts a distally facing end of the first rod, wherein the injector is configured such that the proximally facing end pushes the distally facing end proximally to move the first radially inward protrusion proximally out of the first channel,
   the first probe comprises a flex arm configured to flex to enable distal movement of the first probe and then collide with a distal face of the outer housing assembly to prevent proximal movement of the first probe,
   the outer housing assembly comprises a first groove and a second groove that are oriented from the distal end of the outer housing assembly to a proximal end of the outer housing assembly,
   the first probe comprises a first fin slidably coupled to the first groove, and
   and the first rod comprises a second fin slidably coupled to the second groove.

9. The injector of claim 1, wherein the outer housing assembly comprises a first groove,
   wherein the barrel comprises a first radially outward protrusion located at least partially between the first probe and the second probe such that the first probe and the second probe limit rotation of the first radially outward protrusion relative to a first central axis of the outer housing assembly, and
   wherein the first probe, the second probe, and the first radially outward protrusion are slidably coupled to the first groove having a second central axis that is oriented within ten degrees of parallel to the first central axis.

10. The injector of claim 1, wherein the first probe comprises a distally facing skin-contacting surface, a flex arm, a first radially outward protrusion, and a second radially outward protrusion, and the outer housing assembly comprises a first groove and a second groove,
wherein the flex arm is configured to flex to enable distal movement of the first probe and then collide with a distal face of the outer housing assembly to prevent proximal movement of the first probe, the first radially outward protrusion is slidably coupled to the first groove of the outer housing assembly, and the second radially outward protrusion is slidably coupled to the second groove of the outer housing assembly.

11. The injector of claim 1, wherein the outer housing assembly comprises a first groove, a second groove, a third groove, and a fourth groove,
wherein the first probe is slidably coupled to the first groove, the second probe is slidable coupled to the second groove, the first rod is slidably coupled to the third groove, and the second rod is slidably coupled to the fourth groove such that the first probe, the second probe, the first rod, and the second rod are configured to move proximally relative to the outer housing assembly to enable the plunger to rotate relative to the outer housing assembly.

12. The injector of claim 11, wherein the first probe comprises a first radially outward protrusion that slidably couples the first probe to the first groove,
the second probe comprises a second radially outward protrusion that slidably couples the second probe to the second groove,
the first rod comprises a third radially outward protrusion that slidably couples the first rod to the third groove, and
the second rod comprises a fourth radially outward protrusion that slidably couples the second rod to the fourth groove.

13. The injector of claim 11, wherein the first probe comprises a first L-shaped protrusion that slidably couples the first probe to the first groove,
the second probe comprises a second L-shaped protrusion that slidably couples the second probe to the second groove,
the first rod comprises a first T-shaped protrusion that slidably couples the first rod to the third groove, and
the second rod comprises a second T-shaped protrusion that slidably couples the second rod to the fourth groove.

14. The injector of claim 11, wherein the first groove, the second groove, the third groove, and the fourth groove run from a distal portion of the outer housing assembly to a proximal portion of the outer housing assembly.

15. The injector of claim 11, wherein the outer housing assembly comprises a central axis from a distal portion of the outer housing assembly to a proximal portion of the outer housing assembly, the first groove is oriented in a first direction from the distal portion to the proximal portion, the second groove is oriented in a second direction from the distal portion to the proximal portion, the third groove is oriented in a third direction from the distal portion to the proximal portion, the fourth groove is oriented in a fourth direction from the distal portion to the proximal portion, and the first direction, the second direction, the third direction, and the fourth direction are within ten degrees of parallel to the central axis.

16. An injector comprising:
an outer housing assembly;
a syringe coupled at least partially inside the outer housing assembly and having a barrel, a needle, and a plunger;
a first probe protruding from a distal end of the outer housing assembly;
a second probe protruding from the distal end of the outer housing assembly and configured to move independently of the first probe;
a third probe protruding from the distal end of the outer housing assembly and configured to move independently of the first probe and the second probe;
a first rod slidably coupled to the outer housing assembly and configured such that moving the first probe proximally relative to the outer housing assembly pushes the first rod proximally to unlock the first rod from the plunger;
a second rod slidably coupled to the outer housing assembly and configured to move independently of the first rod such that moving the second probe proximally relative to the outer housing assembly pushes the second rod proximally to unlock the second rod from the plunger;
a third rod slidably coupled to the outer housing assembly and configured to move independently of the first rod and the second rod such that moving the third probe proximally relative to the outer housing assembly pushes the third rod proximally to unlock the third rod from the plunger; and
a first spring configured to push the plunger distally relative to the outer housing assembly, wherein the injector is configured such that unlocking the first rod, the second rod, and the third rod from the plunger enables the plunger to move distally relative to the outer housing assembly such that the first spring pushes the plunger distally relative to the outer housing assembly to inject a medicine.

17. The injector of claim 16, wherein the injector is configured such that after the medicine is injected, the first probe, the second probe, and the third probe move distally relative to the outer housing assembly to form a sheath that blocks a distal end of the needle from punctures.

18. The injector of claim 17, wherein the first probe, the second probe, and the third probe are spaced radially outward around a perimeter of the needle.

19. The injector of claim 16, further comprising a second spring located around at least a first portion of the plunger and compressed between a first radially outward protrusion of the plunger and at least one of the first probe and the second probe, and
the injector further comprising a third spring compressed between a proximal end of the outer housing assembly and at least a second portion of the first rod such that the third spring is configured to push the first rod, the second rod, and the third rod distally relative to the outer housing assembly, wherein the injector is configured such that moving the first probe, the second probe, and the third probe proximally relative to the outer housing assembly to push the first rod, the second rod, and the third rod proximally to unlock the first rod, the second rod, and the third rod from the plunger requires overcoming a spring force of the third spring.

* * * * *